United States Patent
Ling

(10) Patent No.: US 10,155,977 B2
(45) Date of Patent: Dec. 18, 2018

(54) DNA AMPLIFICATION VIA SCISSOR-LIKE STRUCTURES (DASL)

(71) Applicant: GENEBIO SYSTEMS, INC., Toronto (CA)

(72) Inventor: Mingfu Ling, Toronto (CA)

(73) Assignee: GeneBio Systems, Inc., Toronto, Ontario (CA)

( * ) Notice: Subject to any disclaimer, the term of this patent is extended or adjusted under 35 U.S.C. 154(b) by 253 days.

(21) Appl. No.: 14/903,416

(22) PCT Filed: Jul. 31, 2014

(86) PCT No.: PCT/IB2014/063569
§ 371 (c)(1),
(2) Date: Jan. 7, 2016

(87) PCT Pub. No.: WO2015/019247
PCT Pub. Date: Feb. 12, 2015

(65) Prior Publication Data
US 2016/0258008 A1 Sep. 8, 2016

Related U.S. Application Data

(60) Provisional application No. 61/958,886, filed on Aug. 9, 2013.

(51) Int. Cl.
*C12P 19/34* (2006.01)
*C12Q 1/6844* (2018.01)

(52) U.S. Cl.
CPC .................. *C12Q 1/6844* (2013.01)

(58) Field of Classification Search
None
See application file for complete search history.

(56) References Cited

U.S. PATENT DOCUMENTS

| | | | |
|---|---|---|---|
| 5,874,260 A * | 2/1999 | Cleuziat | C12Q 1/6853 435/91.2 |
| 6,117,635 A * | 9/2000 | Nazarenko | C12Q 1/6818 435/6.11 |
| 6,410,278 B1 | 6/2002 | Notomi et al. | |
| 7,803,550 B2 * | 9/2010 | Makarov | C12P 19/34 435/6.1 |
| 2012/0157326 A1 * | 6/2012 | Tisi | C12Q 1/6844 506/7 |

OTHER PUBLICATIONS

International Search Report and Written Opinion dated Nov. 10, 2014 in International (PCT) Application No. PCT/IB2014/063569.

* cited by examiner

*Primary Examiner* — Kenneth R Horlick

(57) ABSTRACT

Methods and systems are provided for amplifying target nucleic acids by means of a polymerase with strand displacement activity, using two or more stem loop primers, each with a 3'-end portion comprising sequence complementary to a target homology site of a target nucleic acid and 5'-end portion with a sequence comprising a stem sequence, a loop sequence and a sequence which is reverse complementary to the stem sequence, the said 5'-end portion being capable of forming a stem loop. Such methods and systems can be used to amplify target nucleic acids isothermally by means of a polymerase with strand displacement activities.

20 Claims, 21 Drawing Sheets

Specification includes a Sequence Listing.

Figure 9

```
  1  ATGGTTCCCA ATAAAAGTGA CTCTCAGCGA GCCTCAATGC TCCCAGTGCT ATTCATGGGC
        FII-NF1              SL        PIA-FII-F2'              PIA-FII-NR2
                                              FII-Nbooster
 61  AGCTCTCTGG GCTCAGGAAG AGCCAGTAAT ACT
        SL       FII-NF1
```

Figure 12

```
1    TTTGGAGAGT AGGGGGCCAC TCATATTCTG GGCTCCTGGA ACCAATCCCG TGAAAGAATT
                    FII-F1                      St.      PIA-FII-F2

61   ATTTTTGTGT TCTAAAACT ATGGTTCCCA ATAAAAGTGA CTCTCAGCGA GCCTCAATGC
                                                        FII-F1'

121  TCCCAGTGCT ATTCATGGGC AGCTCTCTGG GCTCAGGAAG AGCCAGTAAT ACTACTGGAT
          FII-Nbooster    PIA-FII-NR2      St.

181  AAAGAAGACT TAAGAATCCA CCACCTGGTG CACGCTGGTA GTCCGA
              FII-R1
```

Figure 14

```
  1   TTTGGAGAGT AGGGGGCCAC TCATATTCTG GGCTCCTGGA ACCAATCCCG TGAAAGAATT
                           FII-F1

61   ATTTTTGTGT TCTAAAACT ATGGTTCCCA ATAAAAGTGA CTCTCAGCGA GCCTCAATGC
                                                                  SL

121   TCCCAGTGCT ATTCATGGGC AGCTCTCTGG GCTCAGGAAG AGCCAGTAAT ACTACTGGAT
      FII-NBooster    FIA-FII-NR2   SL
      FIA-FII-F2'

181   AAAGAAGACT TAAGAATCCA CCACCTGGTG CACGCTGGTA GTCCGA
                 FII-B1
```

Figure 16

```
  1  TTTGGAGAGT AGGGGGCCAC TCATATTCTG GGCTCCTGGA ACCAATCCCG TGAAAGAATT
                         FII-F1                  SL    PIA-FII-F2-Nu

61  ATTTTTGTGT TTCTAAAACT ATGGTTCCCA ATAAAAGTGA CTCTCAGCGA GCCTCAATGC
                         FII-F1'                                SL

121  TCCCAGTGCT ATTCATGGGC AGCTCTCTGG GCTCAGGAAG AGCCAGTAAT ACTACTGGAT
         FII-Nbooster       PIA-FII-NR2   SL            PIA-FII-R2          SL
       PIA-FII-F2          FII-filler-F'B                  PIA-FII-R2-Nu

181  AAAGAAGACT TAAGAATCCA CCACCTGGTG CACGCTGGTA GTCCGA
              FII-R1
```

Figure 18

```
1    CTATTGGCAG GTTACCCCAA AGGCCACCCC GAAGCAGGGA GCTTTGAGGC TGACCTGAAG
              677-F1                      SL    PIA-677-F2

61   CACTTGAAGG AGAAGGTGTC TGCGGGAGCC GATTTCATCA TCACGCAGCT TTTCTTTGAG
        677-booster 1        677-booster 4         PIA-677-R2          SL 121  GCTGACACAT TCTTCCGCTT TGTGAAGGCA TGCACCGACA TGGGCATCAC T
                              677-R1                              SL
```

DNA AMPLIFICATION VIA SCISSOR-LIKE STRUCTURES (DASL)

FIELD OF THE INVENTION

The present invention relates to amplification of nucleic acids. More specifically, the present invention relates to methods and systems for amplifying nucleic acids using novel primer and amplification designs.

BACKGROUND ART

The amplification of nucleic acids is commonly used in research, forensics, medicine, including diagnostics, and agriculture. One of the best-known amplification methods is the polymerase chain reaction (PCR), which is a target amplification method (See U.S. Pat. Nos. 4,683,195, 4,683, 202 and 4,800,159). A PCR reaction typically utilizes two primers, which are bound to the 5'-end and 3'-end of the target nucleotide sequence and a DNA polymerase which extends the bound primers by adding bases using deoxynucleoside triphosphates (dNTPs) to generate double-stranded products. By raising and lowering the temperature of the reaction mixture, the two strands of the DNA product are separated and serve as templates for the next round of primer binding and extension, and the process is repeated. PCR requires a thermocycler instrumentation to raise and lower the temperature and thus has limitations in some rapid and field testing settings.

Target amplification methods in isothermal environments have been developed in the past few years. One is Strand Displacement Amplification (SDA). SDA combines the ability of a restriction endonuclease to nick the unmodified strand of a target DNA and the action of an exonuclease-deficient DNA polymerase to extend the 3' end at the nick and displace the downstream DNA strand. The displaced strand serves as a template for a complementary strand reaction and vice versa, resulting in amplification of the target DNA (See U.S. Pat. Nos. 5,455,166 and 5,470,723). In the originally-designed SDA, the DNA was first cleaved by a restriction enzyme in order to generate an amplifiable target fragment with defined 5' and 3'-ends but the requirement of a restriction enzyme cleavage site limited the choice of possible target DNA sequences (See for example, Walker et. al., *Proc. Natl. Acad. Sci. USA* 89:392-396 (1992)). SDA was further developed by the addition of bumper primers which flank the region to be amplified (Walker et al. supra (1992), U.S. Pat. No. 5,916,779). SDA technology has been used mainly for clinical diagnosis of infectious diseases such as chlamydia and gonorrhea. However, SDA is inefficient at rapidly amplifying sequences.

Another isothermal amplification system, Transcription-Mediated Amplification (TMA), uses the function of an RNA polymerase to make RNA from a promoter engineered in the primer region, and a reverse transcriptase, to produce DNA from the RNA templates. This RNA amplification technology has been further developed by introducing a third enzymatic activity, RNase H, to remove the RNA from cDNA without the heat-denaturing step. Thus the thermocycling step has been eliminated, generating an isothermal amplification method named Self-Sustained Sequence Replication (3SR) (See, for example, Guatelli et al., *Proc. Natl. Acad. Sci. USA* 87:1874-1878 (1990)). However, the starting material for TMA and 3SR is limited to RNA molecules, and cannot be DNA.

A third isothermal target amplification method, Rolling Circle Amplification (RCA), generates multiple copies of a sequence for the use in in vitro DNA amplification adapted from in vivo rolling circle DNA replication (See Fire and Xu, *Proc. Natl. Acad. Sci. USA* 92:4641-4645 (1995); Lui, et al., *J. Am. Chem. Soc.* 118:1587-1594 (1996); Lizardi, et al., *Nature Genetics* 19:225-232 (1998), U.S. Pat. Nos. 5,714,320 and 6,235,502). A DNA polymerase extends a primer on a circular template generating tandemly linked copies of the complementary sequence of the template (See Kornberg and Baker, DNA Replication, W.H. Freeman and Company, New York ($2^{nd}$ ed. (1992)). Recently, RCA has been further developed in a technique, named Multiple Displacement Amplification (MDA), which generates a more uniform representation in whole genome amplification (See Dean et. al., *Proc. Natl. Acad. Sci. USA* 99:5261-5266 (2002)). However, these methods are inconvenient to use as there is a need to generate a circular template as part of the procedure.

A further isothermal amplification system, loop mediated isothermal amplification (LAMP), uses oligonucleotide primers provided at the 5'-side portion of each primer with a nucleotide sequence that is reverse complementary to a sequence of a region extended with this primer as the origin of extension (Notomi T, et al., 2000. Nucleic Acids Research 28:E63; and U.S. Pat. No. 6,410,278). Amplification proceeds in 45 min to 1 hour and yields a ladder pattern of various products. However, the need to extend the primers with the multiple target regions for both the forward and reverse directions of the template make primer design difficult. LAMP uses turn-back primers which includes a tail region at the 5' end that folds back after the primer binds to the target sequence. Specifically, after the binding of the turn-back primer to the target sequence, the 5' end tail of the turn-back primer will "fold back" and bind to a nucleotide sequence present on the target, thus forming a loop after the 3' end of the turn-back primer binds to the target and is extended. The complementary strand will form another loop with a complementary sequence. Both loops are at least about 80 to 90 base pairs long. In addition, a turn-back primer construct must typically contain at least 80 base pairs of target sequence, excluding the 5'-side portions of the primers, and typically at least 200 base pairs of target sequence, including the 5'-side portions of the primers. Amplifying relatively large products restricts the reaction yield and lengthens reaction time.

Another isothermal amplification system is the Smart Amplification Process 2 (SMAP2) which utilizes a turn-back primer as described in LAMP, a folding primer, two outer primers and a booster primer. Examples are described in Mitani et al, Nature Methods, Vol. 4 No. 3: 257-262 (2007) and Kimura et al, Biochemical and Biophysical Research Communications 383 (2009): 455-459. The folding primer includes a palindromic sequence at the 5' end that causes the formation of a small hairpin structure which is 3 to 15 base pairs long, with the hairpin loop part of the structure being 3-7 bases long.

The potential uses for nucleic acid amplification techniques continue to grow. For example, most nucleic acid assays, including many genotyping assays, utilize amplification reactions. Detection of environmental and food contaminants places demands on sensitivity and analytic power of diagnostic tests, which particularly need nucleic acid amplification procedures. Consequently, improvements in amplification methodology over current technologies are desirable. For example, desired improvements would include nucleic acid amplification methods which take place in isothermal reaction environments, involve convenient design of primers and other starting materials, and are capable of rapidly amplifying relatively smaller nucleic acid sequences.

SUMMARY OF THE INVENTION

The present invention provides methods, systems and kits for exponentially amplifying target nucleic acids, specifically and efficiently, using two or more stem loop primers each with a 3'-end portion comprising a sequence complementary to a target homology site and a 5'-end portion comprising a stem loop, the said stem loop primers are chosen in both strands of the target and in such a manner that the 3' ends of the primers point to each other to amplify the intended target. Such methods, systems and kits can be used to amplify target nucleic acids isothermally with a polymerase with strand displacement activities.

The methods and systems of the present invention can take place in an isothermal reaction environment, and therefore, do not require the use and expense of a thermocycler instrumentation or any other device or techniques for raising or lowering temperature. The materials used in the present invention, including the stem loop primers, are relatively easy and convenient to obtain and/or design. Also, the present invention may be used with only a single type of polymerase enzyme. The methods and systems of the present invention are designed to amplify a wide range of target nucleic acid sequences, including relatively smaller nucleic acid sequences whose amplification generally result in a higher reaction yield and shorter reaction time.

In one aspect, the present invention provides a method of amplifying a nucleic acid comprising:

(a) providing a first template having: (i) a 3' stem loop formed by a first region located 3' terminal and a first complementary region annealing to one another to form a first stem, and a first loop region connecting said first region located 3' terminal and said first complementary region; (ii) a 5' end stem loop formed by a second region located 5' terminal and a second complementary region annealing to one another to form a second stem, and a second loop region connecting said second region located 5' terminal and said second complementary region; and (iii) a single stranded target sequence connecting the 3' end stem loop and the 5' end stem loop, said target sequence having a first homology site at the 3' end of the target sequence, a second homology site at the 5' end of the target sequence and, optionally, a linking region between the first homology site and the second homology site;

(b) providing two or more stem loop primers, a polymerase having strand displacement activity and a reaction buffer; wherein a first stem loop primer has: (i) a 5' end stem loop formed by a third region located 5' terminal and a third complementary region annealing to one another to form a third stem, and a third loop region connecting said third region located 5' terminal and said third complementary region; and (ii) a nucleotide sequence at the 3' terminal complementary to the first homology site; and wherein a second stem loop primer has: (i) a 5' end stem loop formed by a fourth region located 5' terminal and a fourth complementary region annealing to one another to form a fourth stem, and a fourth loop region connecting said fourth region located 5' terminal and said fourth complementary region; and (ii) a nucleotide sequence at the 3' terminal complementary to a sequence which is complementary to the second homology site;

(c) annealing the first stem loop primer to the first homology site on the first template;

(d) extending the first stem loop primer along the first template by means of the polymerase having strand displacement activity to form a second template, said second template having: (i) a third homology site complementary to the first homology site; and (ii) a fourth homology site complementary to the second homology site;

(e) extending the 3' terminal of the first template by means of the polymerase having strand displacement activity, thereby displacing the second template from the first template;

(f) annealing the second stem loop primer to the fourth homology site on the second template;

(g) extending the second stem loop primer along the second template by means of the polymerase having strand displacement activity to form a third template;

(h) extending the 3' terminal of the second template by means of the polymerase having strand displacement activity, thereby displacing the third template from the second template; and (i) repeating steps (c) to (h) using the third template as the first template in step (c), thereby amplifying the nucleic acid.

In another aspect, the present invention provides a system for amplifying nucleic acid comprising:

(a) a first template having: (i) a 3' stem loop formed by a first region located 3' terminal and a first complementary region annealing to one another to form a first stem, and a first loop region connecting said first region located 3' terminal and said first complementary region; (ii) a 5' end stem loop formed by a second region located 5' terminal and a second complementary region annealing to one another to form a second stem, and a second loop region connecting said second region located 5' terminal and said second complementary region; and (iii) a single stranded target sequence connecting the 3' end stem loop and the 5' end stem loop, said target sequence having a first homology site at the 3' end of the target sequence, a second homology site at the 5' end of the target sequence and, optionally, a linking region between the first homology site and the second homology site; and (b) two or more stem loop primers, a polymerase having strand displacement activity and a reaction buffer; wherein a first stem loop primer has: (i) a 5' end stem loop formed by a third region located 5' terminal and a third complementary region annealing to one another to form a third stem, and a third loop region connecting said third region located 5' terminal and said third complementary region; and (ii) a nucleotide sequence at the 3' terminal complementary to the first homology site; and wherein a second stem loop primer has: (i) a 5' end stem loop formed by a fourth region located 5' terminal and a fourth complementary region annealing to one another to form a fourth stem, and a fourth loop region connecting said fourth region located 5' terminal and said fourth complementary region; and (ii) a nucleotide sequence at the 3' terminal complementary to a sequence which is complementary to the second homology site.

Preferably, said method takes place in an isothermal reaction environment.

Preferably, said method further comprises:

(i) providing a displacement primer, wherein said displacement primer has a nucleotide sequence complementary to a nucleotide sequence upstream or downstream of one or more of said homology sites;

(ii) annealing the displacement primer to a complementary region upstream or downstream of one of said homology sites; and (iii) extending the displacement primer by means of the polymerase having strand displacement activity, thereby displacing two of said templates from each other.

Preferably, said method further comprises:

(i) providing a loop primer, wherein said loop primer has a nucleotide sequence complementary to a nucleotide sequence on one of said loop regions of said stem loops on one of said templates;

(ii) annealing the loop primer to a complementary region on one of said loop regions of said stem loops on one of said templates; and (iii) extending the loop primer by means of the polymerase having strand displacement activity, thereby facilitating displacement of two of said templates from each other.

Preferably, said method further comprises:

(i) providing a booster primer, wherein said booster primer has a nucleotide sequence complementary to a nucleotide sequence on said linking region;

(ii) annealing the booster primer to a complementary region on said linking region; and (iii) extending the booster primer by means of the polymerase having strand displacement activity, thereby facilitating displacement of two of said templates from each other.

Preferably, said system operates in an isothermal reaction environment.

Preferably, said system further comprises a displacement primer, wherein said displacement primer has a nucleotide sequence complementary to a nucleotide sequence upstream or downstream of one or more of said homology sites.

Preferably, said system further comprises a loop primer, wherein said loop primer has a nucleotide sequence complementary to a nucleotide sequence on one of said loop regions of said stem loops on the first template.

Preferably, said system further comprises a booster primer, wherein said booster primer has a nucleotide sequence complementary to a nucleotide sequence on said linking region.

Preferably, said polymerase with strand displacement activity is Bst DNA polymerase large fragment.

Preferably, said reaction buffer comprises betaine.

Preferably, said single stranded target sequence has a length of 70 bases pair or fewer.

Preferably, said single stranded target sequence has a length of 50 base pairs or fewer.

Preferably, said 3' end stem loop and said 5' end stem loop of the first template have the same nucleotide sequence.

Preferably, said step (a) of providing said first template comprises:

(a1) providing a double stranded nucleic acid target, said double stranded nucleic acid target comprising a first strand complementary to a second strand, said second strand having sequences which are the same as the sequences of the third and fourth homology sites;

(a2) annealing the second stem loop primer to the sequence which is the same as the fourth homology site on the second strand;

(a3) extending the second stem loop primer along the second strand by means of the polymerase having strand displacement activity to form a third strand, said third strand having sequences which are the same as the sequences of the first and second homology sites, thereby displacing the first strand;

(a4) annealing the first stem loop primer to the sequence which is the same as the first homology site on the third strand;

(a5) extending the first stem loop primer along the third strand by means of the polymerase having strand displacement activity to form a fourth strand, said fourth strand having sequences which are the same as the sequences of the third and fourth homology sites, thereby displacing the second strand;

(a6) annealing the second stem loop primer to the sequence which is the same as the fourth homology site on the fourth strand;

(a7) extending the second stem loop primer along the fourth strand by means of the polymerase having strand displacement activity to form a fifth strand, said fifth strand having sequences which are the same as the sequences of the first and second homology sites, thereby forming a three strand complex having the third, fourth and fifth strands;

(a8) allowing the three strand complex to reversibly dissociate into: (i) the third strand; and (ii) a double stranded complex comprising the fourth and fifth strands, wherein one end of the double stranded complex has a 3' end stem loop on the fourth strand and a 5' end stem loop on the fifth strand;

(a9) extending the 3' terminal of the fourth strand by means of the polymerase having strand displacement activity, thereby displacing the fifth strand, wherein the fifth strand is used as the first template in step (a).

Preferably, each of said third and fourth loop regions are 10 to 30 base pairs in length.

Preferably, each of said third and fourth stems are 4 to 25 base pairs in length.

Preferably, said 5' end stem loops of the first stem loop primer and the second stem loop primer have a melting temperature of 60 degrees Celsius to 80 degrees Celsius.

Preferably, each of said third and fourth loop regions comprise at least 60% pyrimidine bases, more preferably at least 75%.

Preferably, each of said third and fourth loop regions comprise at least 60% purine bases, more preferably at least 75%.

Preferably, each of said third and fourth loop regions comprise at least 60% poly adenine bases, more preferably at least 75%.

Preferably, each of said third and fourth loop regions comprise at least 60% poly thymidine bases more preferably at least 75%.

In one alternative embodiment, the third complementary region and the third loop region of the first stem loop primer overlap with the nucleotide sequence at the 3' terminal complementary to the first homology site.

In one alternative embodiment, the third complementary region of the first stem loop primer overlap with the nucleotide sequence at the 3' terminal complementary to the first homology site.

In one alternative embodiment, the fourth complementary region and the fourth loop region of the second stem loop primer overlap with the nucleotide sequence at the 3' terminal complementary to a sequence which is complementary to the second homology site.

In one alternative embodiment, the fourth complementary region of the first stem loop primer overlap with the nucleotide sequence at the 3' terminal complementary to a sequence which is complementary to the second homology site.

The present invention provides methods and systems of exponentially and rapidly amplifying nucleic acid targets. The present invention has been developed as a low-cost method which can use a single enzyme and involves simple primer designs relative to known reaction methods of nucleic acid extension. The present invention provides a method of extending and amplifying a short nucleic acid which is quick and efficient, namely producing high level of amplified nucleic acid in short time period.

BRIEF DESCRIPTION OF THE DRAWINGS

Further aspects and advantages will become apparent from the following description taken together with the accompanying drawings in which:

FIG. 9 illustrates a preferred embodiment of the present invention, wherein the target sequence comprises human prothrombin gene fragment A (SEQ ID NO:1) and sequence alignment between template and primers is shown;

FIG. 12 illustrates a preferred embodiment of the present invention, wherein the target sequence comprises human prothrombin gene fragment B (SEQ ID NO:9) and sequence alignment between template and primers is shown;

FIG. 14 illustrates another preferred embodiment of the present invention, wherein the target sequence comprises human prothrombin gene fragment B (SEQ ID NO:9) and sequence alignment between template and primers is shown;

FIG. 16 illustrates yet another preferred embodiment of the present invention, wherein the target sequence comprises human prothrombin gene fragment B (SEQ ID NO:9) and sequence alignment between template and primers is shown;

FIG. 18 illustrates another preferred embodiment of the present invention, wherein the target sequence comprises human methylenetetrahydrofolate reductase (MTHFR) fragment (SEQ ID NO:21) and sequence alignment between template and primers is shown;

Throughout all the drawings and the description, similar parts are indicated by the same reference numerals.

DETAILED DESCRIPTION OF THE PREFERRED EMBODIMENTS

Figure 1:
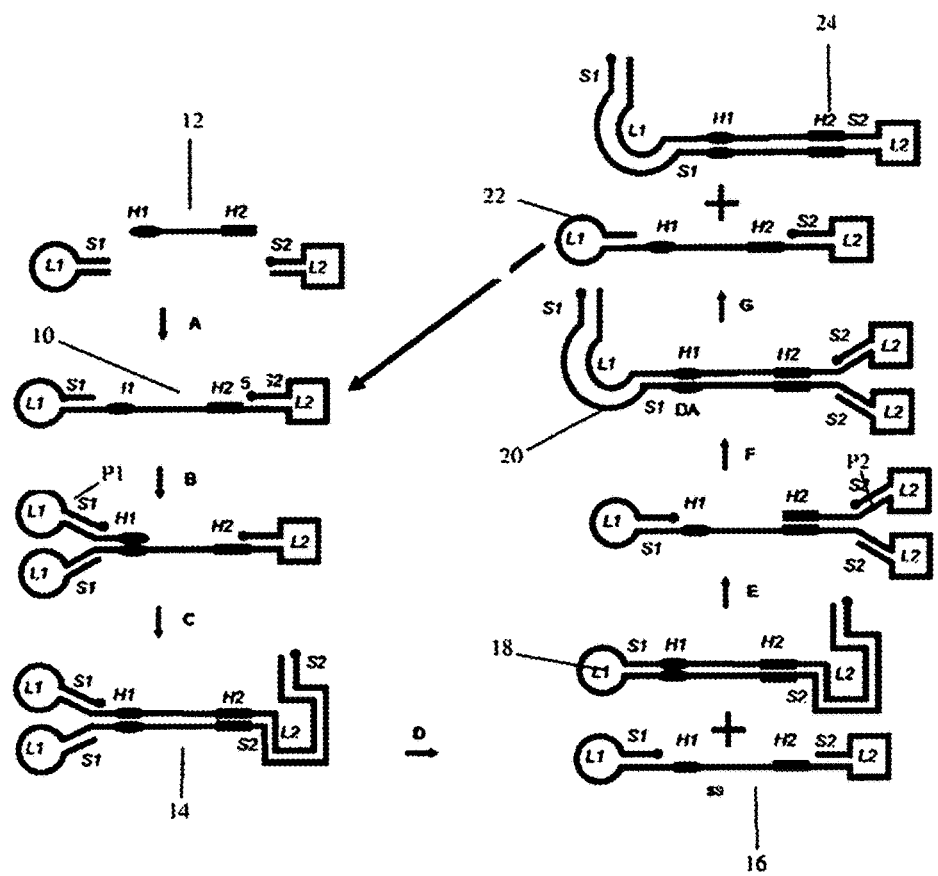
FIG. 1 illustrates a nucleic acid amplification pathway in accordance with one preferred embodiment of the present invention.

The methods and systems of the present invention will now be described with respect to preferred embodiments. The methods of the present invention may be herein referred to as DNA Amplification via Scissor-Like Structures (DASL). Reference is made to FIGS. 1 to 21 which relate to preferred embodiments of the present invention.

Definitions

For convenience, certain terms employed in the specification, examples and appended claims are defined here. The definitions are provided for the entire description, unless an excepted definition is specifically provided.

The term "nucleic acid" refers to double stranded or single stranded DNA, RNA molecules or DNA/RNA hybrids. These molecules may be nicked or intact as found in living cells. The double stranded or single stranded nucleic acid molecules may be linear or circular. The duplexes may be blunt ended or have single stranded tails, for example, with sticky ends created by restriction endonucleases.

The terms "target nucleic acid, target DNA, target region or target" refer to a whole or part of nucleic acid to be selectively amplified. The target nucleic acid may also be referred to as a fragment or sequence that is intended to be amplified. The size of the target nucleic acid to be amplified may be, for example, in the range of from about 30 bp to 10000 bp, or as large as about 100 kb, or even as large as the entire human genome. The target nucleic acid may be pure in having one type of DNA or RNA, or alternatively may be a mixture of different types and varying length of nucleic acid. The target nucleic acid may be biological or extended, pure or mixed with other biological and cellular materials such as protein, lipids and carbohydrates. The target DNA may be isolated from a variety of sources including the environment, food, agriculture, fermentations, biological fluids such as blood, plasma, serum, milk, cerebrospinal fluid, sputum, saliva, stool, lung aspirates, swabs of mucosal tissues or tissue samples or cells, or skins, or swabs of various surfaces such as medical equipment or door knobs. Nucleic acid samples may be obtained from cells or viruses and may include any of: chromosomal DNA, extra chromosomal DNA including mitochondrial DNA, plasmid DNA, recombinant DNA, DNA fragments, messenger RNA, transfer RNA, ribosomal RNA, double stranded RNA, micro-RNA (miRNA) and small interfering RNA (siRNA) or other RNAs that occur in cells or viruses.

The term "template" refers to part or entirety of a target, or a nucleic acid containing a target to which primers and enzymes bind for the purpose of DNA extension. Templates serve as the reference copy for DNA extension or replication. The term "template" when used in contrast to "target", means the nucleic acid that is modified from, or extended based on, the original target, whereas the "target" means the DNA that is originally found in the sample or before the DASL begins. Template DNA can include non-target sequences that are introduced during or prior to a DASL reaction. For example, externally added stem loop sequence(s), or dimerized, trimized or multimerized sequence(s) may be added to a target to obtain a template.

The term "strand" means one of the chains of the double stranded DNA molecules or the only chain of a RNA or single stranded DNA molecule. For every strand, there can be a complementary strand.

When two DNA strands have complementary sequences, the two strands are said to be complementary. One strand is the "complementary strand" of the other. One strand and its complementary strand are hybridized based on the DNA base pairing, or Watson-Crick, principle, in other words, A, C, G and T (or U) bases pair non-covalently with T, G, C and A bases, respectively.

The terms "forward strand" and "reverse strand" refer to the two mutually complementary strands of a double stranded DNA in a specific configuration. When the two strands are stacked up vertically on each other, as shown in some of the drawings, the top strand is generally conceived to be the forward strand or written by having its 5'-end on the left side and 3'-end on the right side. At the same time, the bottom strand is typically conceived to be the reverse strand or written by having its 3'-end on the left side and 5'-end on the right side, unless otherwise mentioned. In this description, the "reverse strand" is meaningful relative to the "forward strand", vice versa. These terms are used for the clarity and convenience of describing the invention and its preferred embodiments.

The term "strandedness" refers to if the DNA strand is forward or reverse. For example, if two DNA molecules both carry forward strand sequence, they are said to have the same strandedness.

The terms "5'-end" and "3'-end" each refers to a region located at the left or right boundaries of a DNA molecule, including a target, template or a primer. More specifically, 50 to 200 nucleotides, or at least 5 nucleotides from either end of a single strand may be included in the terms "3'-end" and "5'-end". The "3'-end" is the side of the DNA that is extendable, namely to which deoxynucleotide bases can be added by polymerase reactions, provided that the 3'-end is bound to another strand or region of DNA in a fashion to permit such extension to occur. For example, when the 3'-end of a DNA strand forms a stem loop structure, the 3'-end binds to a region of the same strand. Such an end is referred to as the "3'-extendable end". In the presence of suitable conditions such as in the inclusion of a suitable polymerase, dNTP, and buffers, the 3' end can be extended by adding nucleotides in a polymerization reaction. As another example, when the 3'-end of a primer binds to a template, the 3'-end is extendable. The "5'-end" is the opposite end of "3'-end", and is not extendable.

Either "5'-end" or "3'-end" of single or double stranded DNAs may include a stem loop structure. Further, some ends of DNA may contain two side-by-side stem loops, also referred to as the scissor-like structures, one loop for each of the two DNA strands leading to the stem loops.

Each single-stranded DNA has a 5'-end and a 3'-end. Some DNA molecules may have single-stranded regions and double-stranded regions, and such DNAs may be referred to as hybrid DNA.

In referring to relative locations of two different regions of the target or template DNA, a region is upstream when it is closer to the 5'-end relative to another region. Conversely, a region is downstream when it is closer to the 3'-end relative to another region.

The term "same" when used in sequence context means being homologous to another sequence. It does not necessarily mean the sequences must be identical. That is, the sequence of a DNA is said to be homologous to another if both DNA are complementary to and can bind to, a third DNA. Those skilled in the art know that in order to bind a primer to its complementary sequence, some mismatches/insertions/deletions can be tolerated. In general, at least 80% homology is preferred, and at least 90% of homology is more preferred between two homologous sequences.

A homology site of a target is a region which sequence can be used as a DASL primer's target binding sequence located at the 3' portion of such a primer. For example, a forward DASL primer may be designed by using the sequence of a first homology site and a reverse DASL primer may be designed by using the reverse complement of a second homology site.

The complementary sequence means a sequence capable of binding to another sequence under certain conditions to provide a 3'-end serving as the origin of extension of complementary strand, using the other sequence as a template. Those skilled in the art know that in order to bind a primer to its complementary sequence, some mismatches/insertions/deletions in sequence can be tolerated. In general, at least 80% homology/or being complementary is preferred, and at least 90% of homology/or being complementary is more preferred between a primer and a template. Homology and complementarity can be determined based on known algorithms such as BLAST (Altschul, S. F., Gish, W., Miller, W., Myers, E. W. & Lipman, D. J. (1990) "Basic local alignment search tool" J. Mol. Biol. 215:403-410.).

The term "primer" refers to a single stranded nucleic acid, often referred to alternatively as "oligonucleotide primer", capable of binding to a strand of a target nucleic acid, and providing the 3'-end which can become the origin of polymerase-dependent DNA replication/extension of the target nucleic acid. Primers are typically chemically synthesized. The backbone of primers is not necessarily limited to the one via phosphodiester linkages, although this is the most common linkage type. For example, it may be composed of a phosphothioate derivative having S in place of O as a backbone or a peptide nucleic acid based on peptide linkages. The bases may be those capable of complementary base pairing. There are 5 naturally occurring bases, that is, A, C, T, G and U, but a base can be an analogue or modified base such as bromodeoxyuridine wherein the modification does not prevent binding of the primer to the nucleic acid or elongation of the primer or denaturation of double stranded molecules.

The terms "forward primer" and "reverse primer" as used to refer to primers which bind to the reverse and forward strands of template, respectively.

The term "pairing primers" refers to two or more primers which comprise a) a forward primer binding to the reverse strand of template DNA, and b) a reverse primer binding to the forward strand of template, in such a manner that the 3'ends of the two pairing primers face each other and an amplification reaction can occur by binding one of the pairing primers to the extension product of the other of the pairing primers and vice versa. When there are three or more primer comprising a pair of pairing primers, this group of primers are referred to as pairing primers.

Each of the primers according to this invention may have a "stem loop" at the 5' end and a target binding portion at the 3'-end. A stem loop or also referred to as stem loop region or stem loop structure, refers to a structure formed between two regions which are reverse complementary to each other and linked by a linking region, and can bind to each other to form a double stranded structure "stem". As a result of forming a stem, the third region is left single stranded, resulting in the loop region. The stem loops introduced by the primers as mentioned here are incorporated into extended DNA products. As these DNAs serve as templates for further DNA extension, complementary strands are generated. These complementary strands carry new stem loop structures. The new stem loops have the complementary sequence to the stem loops on the primers.

The terms "melting", "dissociating", "denaturing" or "opening" refer to separating all or part of two complementary strands into two single strands in such a way that primers can bind to one of the two strands and can be extended by polymerases. Alternatively, the terms can mean separating two regions of a single DNA strand which are bound to each other, for example to melt the two regions of a stem of a stem loop structure.

The terms "binding", or "annealing" refer to contacting and hybridizing a primer to a region of the single-stranded nucleic acid template under the conditions in which a primer binds only specifically to its complementary sequence on the template strand. In addition, the terms "binding", "annealing" or "closing" may refer to binding occurring between two DNA strands or two regions of a DNA. The specificity of binding may be influenced by the length of the primer or DNA region, the temperature in which the binding reaction is performed, the ionic strength, the pH, temperatures and solvents and metal ions such as magnesium.

The term "reaction" refers to the events involving primers, targets, and templates, including melting, binding, extension, strand displacement and amplification of nucleic acids. The reaction can also be used to refer to a system or container in which reaction occurs.

The term "extension" of nucleic acid is used to describe the lengthening of a 3'extendable end of a primer or a template by DNA extension. If this extension occurs continuously for a significant period of time or a significant number of rounds, a significant amount of specific nucleic acid is accumulated relative to the target nucleic acid. The series of reaction events leading to the accumulation is comprehensively referred to as "amplification".

The term "strand displacement" refers to the separation of a DNA strand from its original complementary strand of a double-stranded DNA or DNA region by an advancing new strand which is being extended using the original complementary strand as the template strand. Some enzymes such as Bst DNA polymerase have strand displacement activity, whereas other enzymes such as Taq DNA polymerase, do not have significant levels of this activity.

Figure 3:
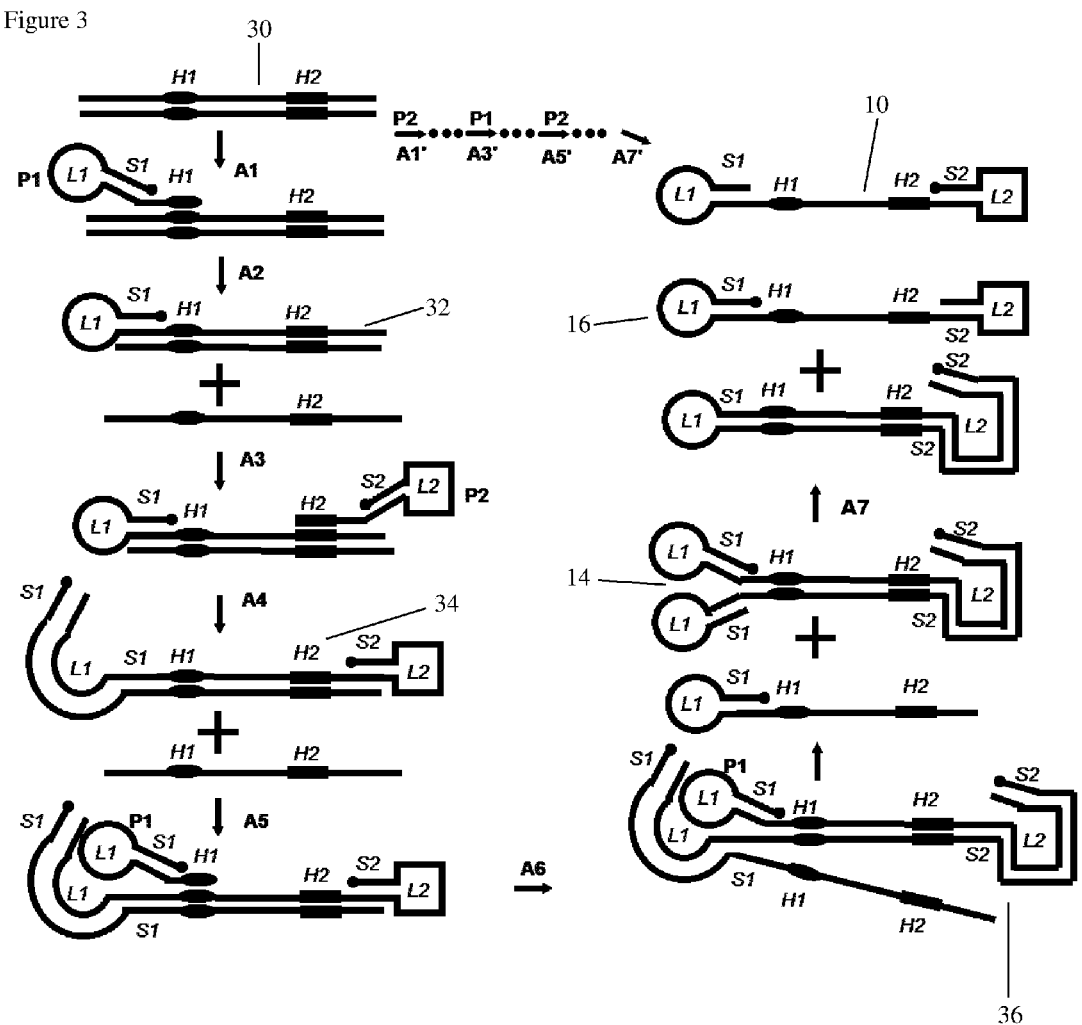
FIG. 3 illustrates the generation of single-stranded target DNA templates in accordance with a preferred embodiment of the present invention.
Figure 4:
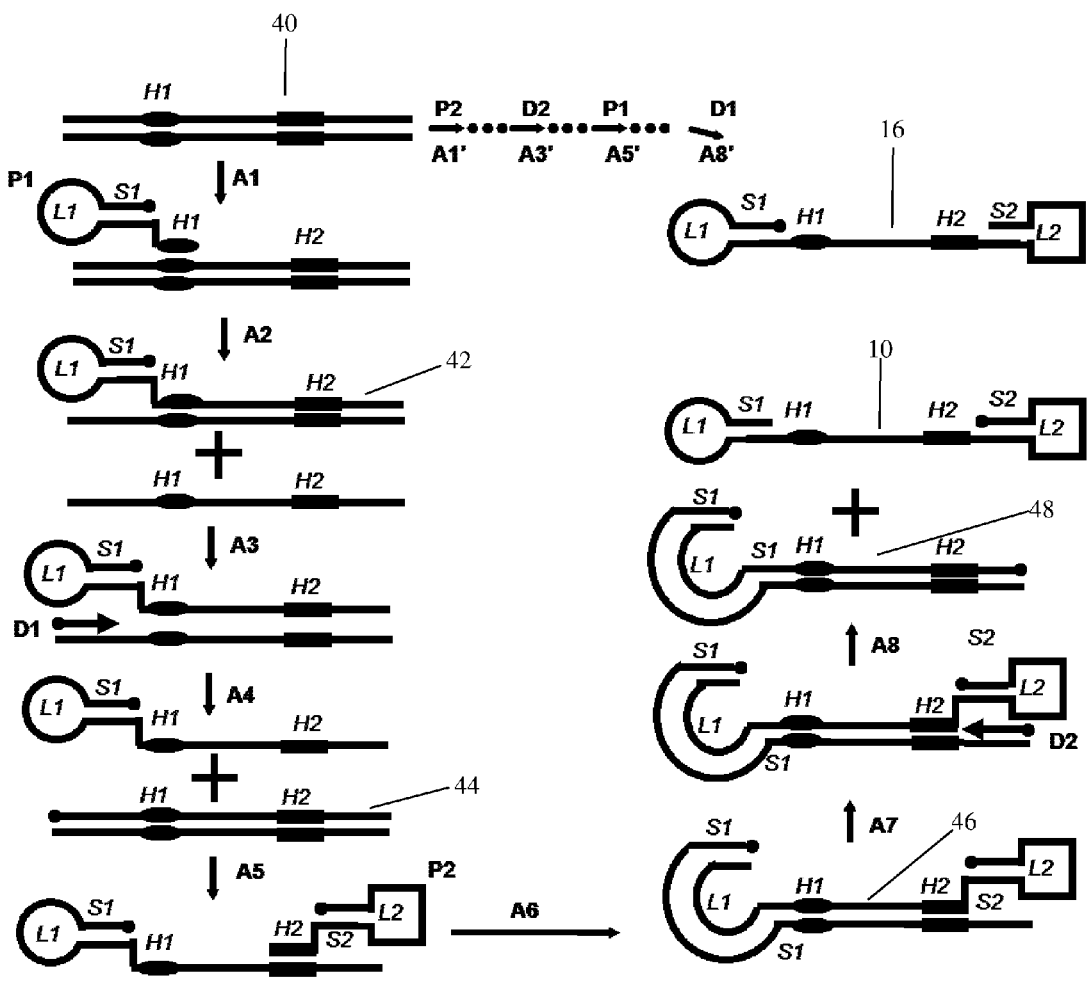
FIG. 4 shows the use of displacement primers in a preferred embodiment of the present invention.

"Isothermal amplification" refers to amplification which occurs about the same incubation temperature for the entire reaction. This does not include the single brief time period (usually 30 s to 2 min, typically less than 15 minutes) prior to the initiation of amplification which may be conducted at a temperature higher than isothermal amplification temperature. A reaction of isothermal amplification refers to the accumulation of amplified DNA products where a template is present. In order to determine how fast a reaction progresses, the time from beginning of the reaction to the end where amplified products are significantly accumulated or no long exponentially increase over time may be referred to as the reaction time. The amount of DNA amplified relative to the amount of template used is sometimes referred to as reaction yield. DASL methods and how they work Referring to FIG. 1, which illustrates the basis of a DASL amplification process, starting with step A, a single stranded DNA 10 which production is described in more details in FIGS. 3 and 4, is provided. This single stranded DNA 10 is characterized from its 3'-end to the 5'-end, as having a first loop L1, a first stem S1, the homology site 1 (H1), a linking target, homology site 2 (H2), a second stem S2 and a second loop L2. In this figure and subsequent figures, a round dot attached to a line denotes a 5' end of a primer or template DNA sequence.

In step B, a DASL primer P1 having the sequence to form the third stem loop L1-S1 and a 3'-end sequence complementary to bind to H1 on the target DNA, binds to the single-stranded DNA 10 in step A.

In step C, the 3'-end of the DASL primer P1 is extended in the isothermal reaction which contains a DNA polymerase, with strand displacement activity, and dNTP and suitable ionic and other buffer conditions. The product of this extension, a DASL DNA 14, is a mostly double stranded DNA with two L1-S1 stem-loops at its 5'-end, one of the S1 stems having an extendable 3'-end, and the other stem has a 5'-end (denoted by a dot). This structure is referred to as the DASL DNA 14 where the double loop is referred to as a scissor-like structure, resembling the handle of a pair of scissors, and the other end with the S2 region, and L2 region and a S2 region, all double stranded, resembling the cutting edges of a pair of scissors.

In step D, the extendable 3'-end of the double loop structure produced in step C, is extended under the isothermal reaction conditions, by means of a polymerase with strand displacement activity. The extension displaces the top strand of the DASL DNA 14, resulting in second type of single stranded DNA 16. Single-stranded DNA 14 and single-stranded DNA 16 are similar in structure, except that they are different in strandedness. The extension creates another product, a mostly double stranded DNA 18, which 5' has a closed loop, which originates from loop 1 (L1) and which 3'-end has a regular double stranded structure characterized with all double stranded regions of H2, S2, L2 and S2.

In step E, the single-stranded DNA 16 is bound by a second DASL primer P2 having a) a 5'-end L2-S2 stem loop and b) a 3'-end sequence complementary to the H2 region on the target DNA.

In step F, primer P2 in step E is extended under the isothermal reaction conditions, forming the second type of DASL DNA 20 which is characterized with the same characteristics as DASL DNA 14 in step C, having an extendable 3'-end on a double loop on the 3'-end, except that the strandedness of DASL DNA 14 and DASL DNA 20 are different.

In step G, the extendable 3'-end of the DASL DNA 20, is extended under the isothermal reaction conditions by means of a polymerase with strand displacement activity. The extension displaces the top strand of the DASL DNA 20 in step F, resulting in a new molecule of single-stranded DNA 22. The extension creates another product, a mostly double stranded DNA 24, which a) has a closed loop 3' end, which originates from loop 2 (L2) and b) has a regular double stranded structure characterized as H1, S1, L1 and S1at the 5'-end. The single-stranded DNA 22 has the identical structure as the starting structure in step B, thus completing a full cycle of amplification. Continued cycling accumulates increased amounts of DNA templates and products, including DASL DNA 18 and 24, leading to amplification.

It should be noted that step B should in general precede step C. The precedence of step B over step C in time sequence is because of the way single-stranded DNA 10 or single-stranded DNA 16 are generated (FIG. 3 and FIG. 4): the H1 or H2 region is released as single stranded template, and thus available for DASL primer binding and extension, earlier than the extendable 3' S1 or S2 end is formed. Nonetheless, the two steps may not be simply sequential. In other words, before the strand extension in step B is complete, the 3'-end of the extendable end may begin its extension in step C.

Figure 2:
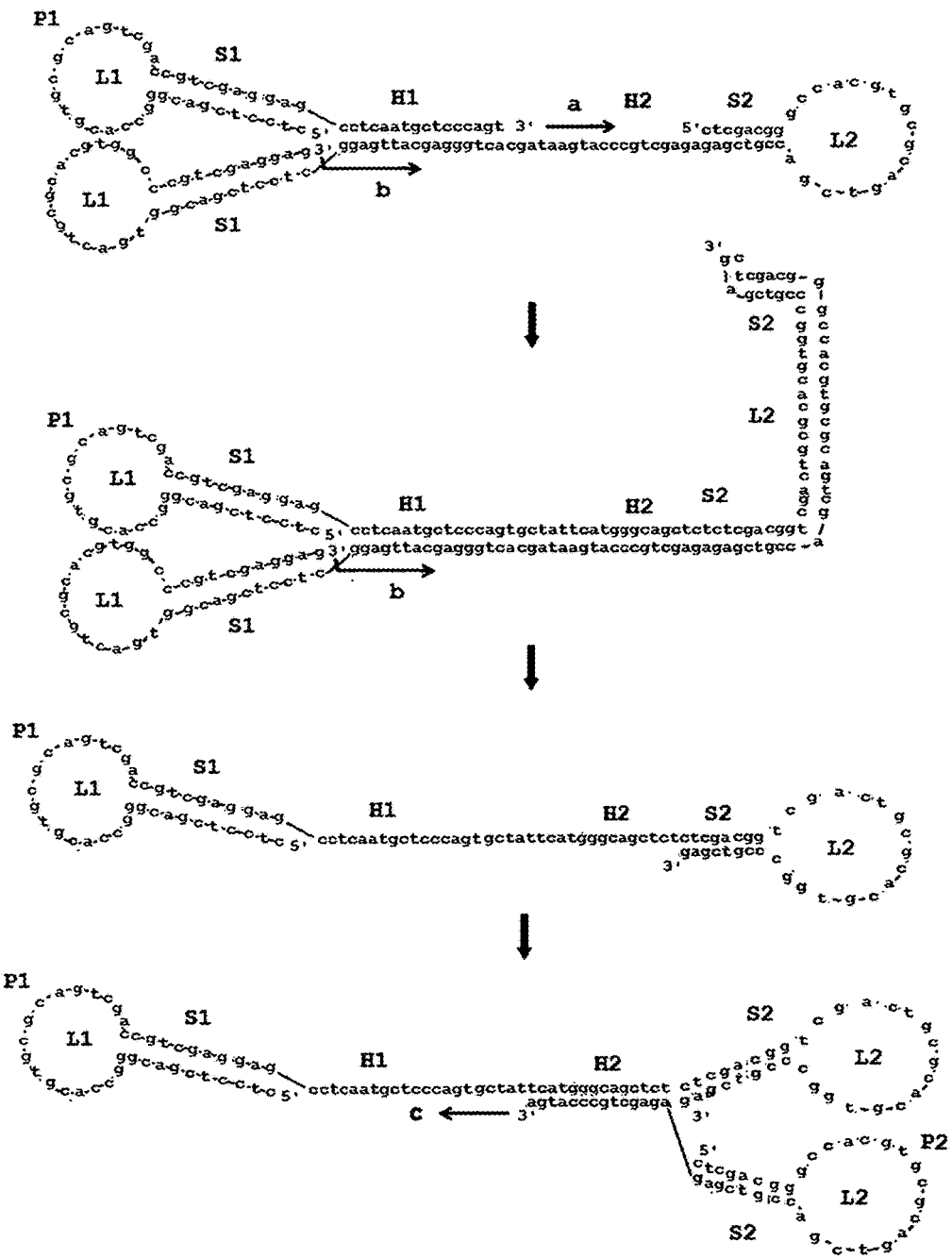
FIG. 2 illustrates steps B, C, D, and E of FIG. 1, including examples of preferred DNA sequences for the template and stem loop primers.

To illustrate the DNA in steps B, C, D and E in FIG. 1, especially the double stem loop ("scissor-like structures") structure and the 3'-end extension in more detail, the examples of such structures and extension are provided with specific sequence in FIG. 2. The template and DASL primers in Example 1 (FIG. 9) are used as the specific sequences. The top panel shows the binding of a first DASL primer P1 to a single-stranded DNA 10. After the DASL primer P1 is extended at the 3'-end, at the 3' extendable end marked by the letter "a" above an arrow, the DASL DNA 14 is formed, shown at the bottom panel. The letter "b" below another arrow illustrates the 3'-extensable end of a double loop structure, which can be extended in the same reaction extending the primer initiation extension "a". Following extension "a", the extension of "b" is completed, leading to a single stranded DNA 16 with stem loops on both ends. This DNA can be the subject of binding by a second DASL primer P2 that pairs with the first DASL primer P1, which end can be extended as marked by the letter "c" beside an arrow.

Referring to FIG. 3, which illustrates a process of generating the single-stranded DNA 10 (step A of FIG. 1), which is a subject a DASL amplification process, in step A1, a DASL primer P1 having the sequence to form the L1-S1 stem loop and a 3'-end sequence complementary to homology site 1 H1 on the target DNA, binds to the reverse strand of the two strands of a target DNA 30.

In step A2, the 3'-end of the primer P1 is extended in the isothermal reaction which contains a DNA polymerase, e.g., Bst DNA polymerase having strand displacement activity, and dNTP and suitable ionic and other buffer conditions, to form a forward template extension strand 32, and displacing the forward strand of the target DNA 30.

In step A3, a reverse primer P2 which has a sequence complementary to homology site 2 H2 at the 3'-end and a stem loop (S2-L2) in its 5'-end, binds to the forward strand in step A2.

In step A4, the 3'-end of the bound primer P2 in step A3 is extended by means of a polymerase having strand displacement activity, to form a template extension strand 34 within a double stranded DNA, and displacing the forward strand of the target DNA.

In step A5, the forward primer P1, as in step A1, binds to the reverse strand of the double stranded DNA in step A4.

In step A6, the 3'-end of the bound primer in step A5 is extended by means of a polymerase having strand displacement activity, to form a forward template extension strand, and forming a three-strand complex 36 among the newly extended template strand and both strands from step A5, as illustrated. Under the isothermal reaction conditions of this invention, the said complex is reversibly dissociated into a single stranded DNA and a double stranded DNA, which has two side-by-side stem loops on the 5'-end, and one of the said loops has an extendable 3'-end, and a 3'-end consisting of H2, S2, L2 and S2 regions all double stranded. This double stranded DNA is referred to as DASL DNA 14.

In step A7, the extendable 3'-end of the DASL DNA 14 is extended by means of a polymerase having strand displacement activity, to displace a single stranded DNA, single-stranded DNA 16. By following parallel steps A1' to A7', another single stranded DNA, single-stranded DNA 10 may be formed. These single stranded DNAs are the subject of amplification methods of this invention (see FIG. 5 and FIG. 6).

If the target DNA 30 in step A1 is single-stranded or cDNA bound to RNA, the above process works similarly except 1) step A1, or step A1', starting with binding a P1 or P2 DASL primer to the reverse or forward single stranded template with the same stem-loop and homology site structure as mentioned above; 2) the extension at step A2 does not displace any DNA strand; 3) the end product generated is one of the two single stranded DNAs, single-stranded DNA 10 or single-stranded DNA 16, rather than both if the target DNA is double stranded. Having either single-stranded DNA 10 template or single-stranded DNA 16 template sustains the amplification, as does having both templates (see FIG. 5).

Referring to FIG. 4, which illustrates another process of generating the single-stranded DNA 10 and single-stranded DNA 16 (step A of FIG. 1), facilitated by displacement primers, in step A1, a DASL primer P1 having sequence capable of forming the L1-S1 stem loop and a 3'-end sequence complementary to H1 on the target DNA, binds to the reverse strand of the two strands of a target DNA 40.

In step A2, the 3'-end of the DASL primer P1 is extended in the isothermal reaction which contains a DNA polymerase having strand displacement activity, and dNTP and suitable ionic and other buffer conditions, to form a forward template extension strand 42, and displacing the forward strand of the target DNA.

In step A3, the reverse strand of the target DNA in step A2 is bound with a forward primer D1, which binds to the region upstream of the forward primer P1 in step A1;

In step A4, the 3'-end of the bound primer D1 in step A3 is extended by means of a polymerase having strand displacement activity, to form a template extension strand 44, and displacing the forward strand extended in step A2, the said stranding being single-stranded;

In step A5, the single-stranded strand in step A4 is bound with the a reverse DASL primer P2 which has a sequence complementary to target homology site 2 at the 3'-end and a sequence capable of forming stem loop S2-L2 in its 5'-end.

In step A6, the 3'-end of the bound primer P2 in step A5 is extended by means of a polymerase having strand displacement activity, to form a template extension strand 46.

In step A7, the forward strand of the DNA in step A6 is bound with a reverse primer D2 which binds to the region downstream of homology site 2, H2, of the target, in step A6.

In step A8, the 3'-end of the bound primer D2 in step A7 is extended by means of a polymerase having strand displacement activity, to form a template extension strand 48, and displacing the reverse strand, the said reverse strand being a single-stranded DNA 10. This single stranded DNA 10 has a loop originating from the forward primer P1 and another originating from the reverse primer P2 from above steps A1 and A5. This said single stranded DNA 10 becomes the subject of amplification methods of this invention (see for example, FIGS. 5 and 6).

If the target DNA in step A1 is single-stranded or cDNA bound to RNA, the above process works similarly except 1) step A1, or step A1': starting with binding a P1 or P2 DASL primer to the reverse or forward single stranded template with the same stem-loop and homology site structure as mentioned above; 2) the extension at step A2 does not displace any DNA strand; 3) the end product generated is one of the two single stranded DNAs, single-stranded DNA 10 or single-stranded DNA 16, rather than both if the target DNA is double stranded. Having either single-stranded DNA 10 template or single-stranded DNA 16 template sustains the amplification, as does having both templates (see FIG. 5).

Figure 5:
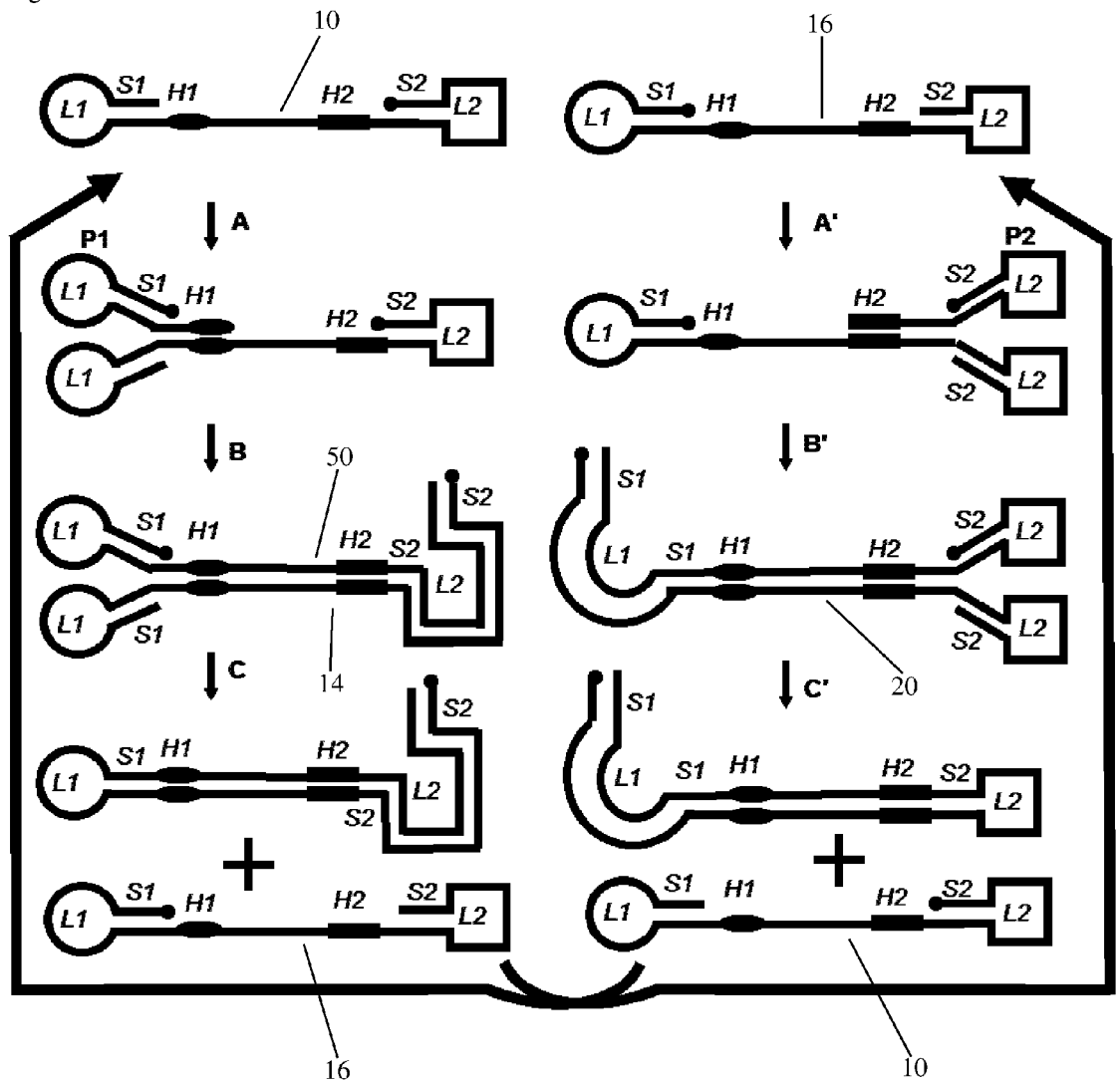
FIG. 5 illustrates a nucleic acid amplification pathway in accordance with a preferred embodiment of the present invention where two single-stranded DNA templates are used.

Referring to FIG. 5, which illustrates an amplification pathway of amplifying simultaneously single-stranded DNA 10 and single-stranded DNA 16, starting in step A, primer P1 with sequence capable of forming stem loop S1-L1 at its 5'-end and sequence complementary to target homology site 1 H1 at 3'-end, binds to the single-stranded DNA 10.

In step B, the bound primer P1 is extended by means of a polymerase having strand displacement activity, to form a template extension strand 50. The double stranded DNA is referred to as a DASL DNA 14. DASL DNA 14 is characterized by the presence of the 3'extendable end at one of the double loops at the 5'-end.

In step C, the 3'extendable end of the DASL DNA 14 in step B is extended, by means of a polymerase having strand displacement activity to form a double stranded DNA with loop L1 on the 5'-end and a regular double-stranded end, at the 3'-end. The extension also displaces and releases a single-stranded DNA, single-stranded DNA 16, which is like the mirror images of the single-stranded DNA 10, at the beginning of the FIG. 5. This second DASL single-stranded DNA 16 is fed into a series of steps A', B' and C', which are similar to the steps A, B and C. Indeed, the products of these two branches, A-C and A'-C', of the amplification pathways feed each other with new templates for further amplification, and thus sustaining a two-strand cyclic amplification process.

Figure 6:
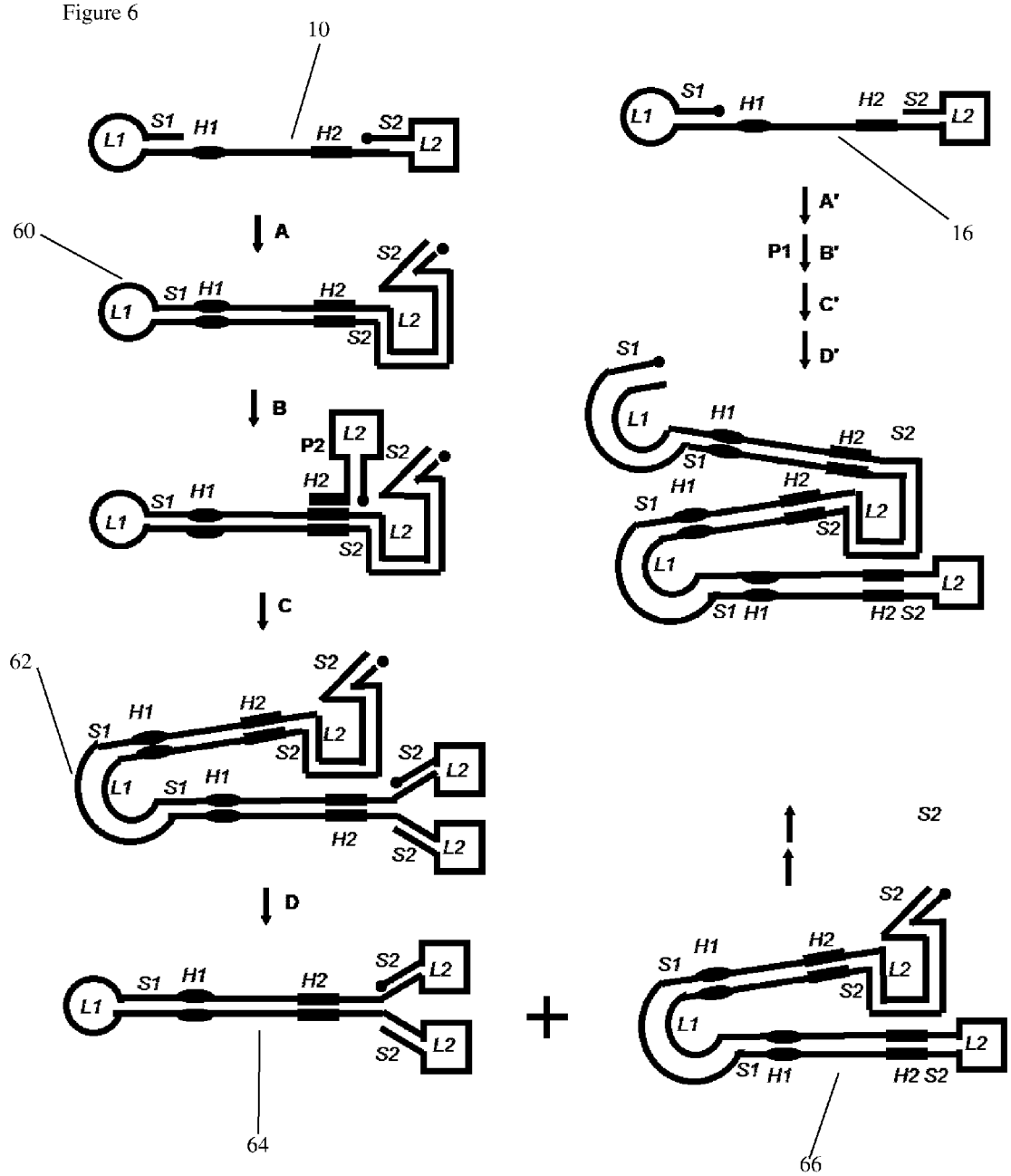
FIG. 6 illustrates a nucleic acid amplification pathway in accordance with another preferred embodiment of the present invention.

Referring to FIG. 6, which illustrates another amplification pathway of amplifying the single-stranded DNA 10 and single-stranded DNA 16 and some related double stranded products, starting in step A, the 3'-extendable end of a single-stranded DNA 10 with loop L1, stem S1, homology site 1 H1, linking region 12, homology site 2 H2, stem S2 and loop L2, is extended by means of a polymerase having strand displacement activity, to form a double stranded DNA 60 with loop L1 on its 5'-end, followed by S1, homology site 1 H1, linking region, homology site 2 H2, and stem S2 sequence, loop L2 sequence and a S2 sequence at its 3'-end. Note that the stem and loop sequences at the 3'-end do not form the stem loop structure, as the sequences are double stranded. This DNA is also an intermediate product of the amplification pathway illustrated in FIG. 5.

In step B, one strand of the double stranded DNA 60 from step A, is bound by primer P2 which has from its 5'-end a sequence capable of forming stem loop L2-S2 and a sequence complementary to target homology site 2 H2 at the 3'-end.

In step C, the primer P2 is extended by means of a polymerase having strand displacement activity, to form the double stranded DNA structure 62, with two serially joined units of the original DASL DNA, i.e., two sets of homology sites H1 and H2 and stem loops, in the form of 5'-S2-L2-S2-H2-H1-S1-L1-S1-H1-H2 followed by double S2-L2 stem loops at the 3'-end. Note that at the 3'-end, there is the double stem loop structure both with the same loop sequence as the loop L2 from primer P2. Also, the two units of the DASL DNA are repeated in a trans-direction, that is, the first unit has the reverse complementary sequence to that of the second unit. Also of note, at the junction site between the two units, there is only one loop sequence, for example one L1 sequence in the structure show for step C.

In step D, the extendable 3'-end of the structure 62 in step C, is extended by means of a polymerase having strand displacement activity, resulting in two double stranded DNAs 64 and 66, one 64 with one unit of DASL DNA or one set of H1-H2 homology sites, and another 66 with two units of DASL DNA sequence, or two sets of H1-H2 homology sites, as shown in step D.

By using the products in step D and continuing in steps similar to steps A through D, DNA products with three units or more units of DASL DNA structures can be produced as illustrated by the dual arrow.

By following steps A' to D' etc., similar to steps A to D and the dual arrow, additional DNA products are generated with structures similar (like mirror images) to those illustrated in FIG. 6.

Figure 7:
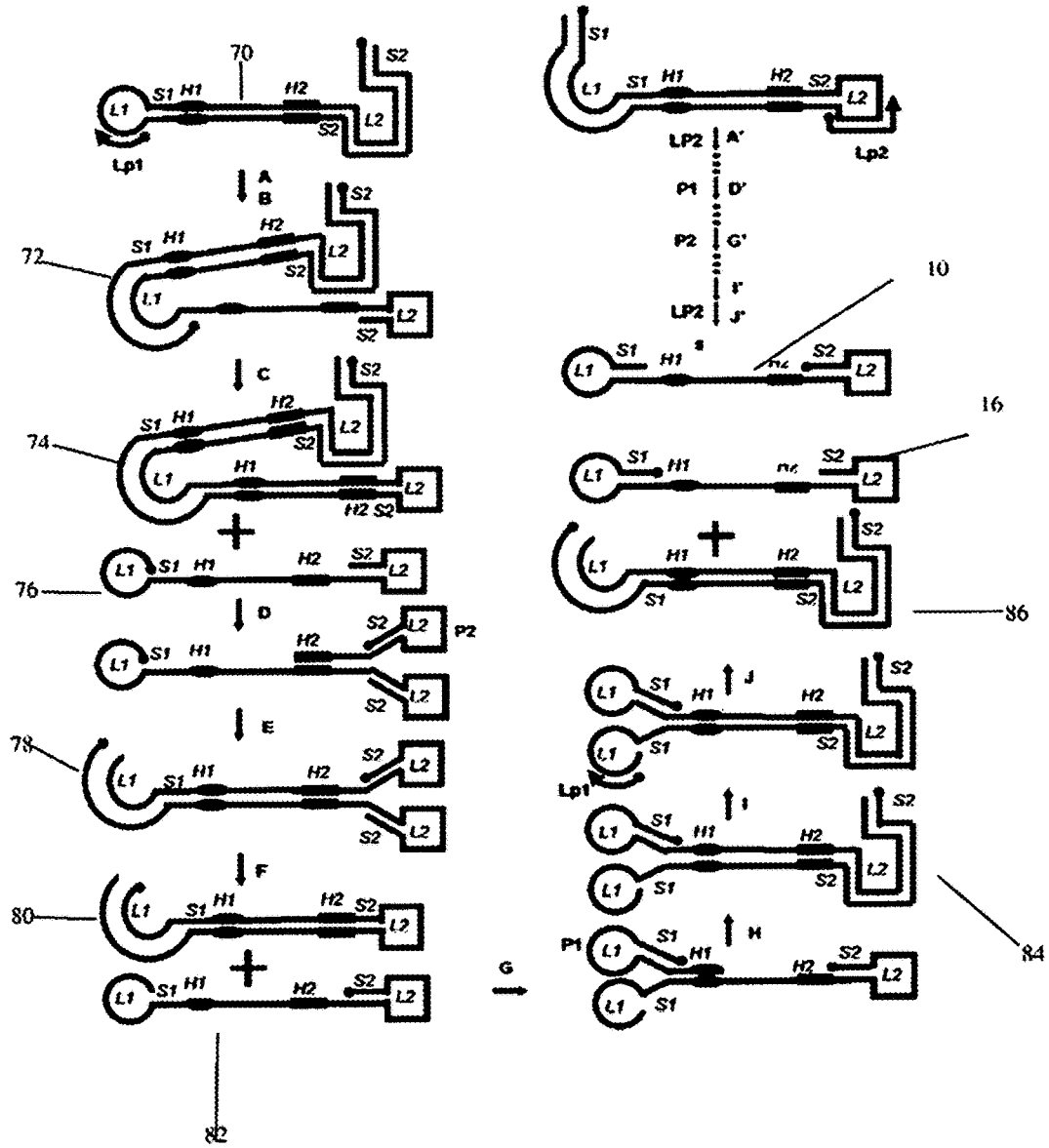
FIG. 7 shows the use of loop primers in a preferred embodiment of the present invention.

Referring to FIG. 7, which illustrates the process of loop primers facilitating a DASL amplification processes, starting in step A, a loop primer Lp1 binds to a double stranded DNA 70, which is a by-product or intermediate product of amplification pathways such as those illustrated in FIGS. 5 and 6. This DNA 70 is double stranded with a loop L1 at the 5'-end, followed by stem S1, homology site 1 H1, linking region, homology site 2 H2, and ends at 3'-end with a stem sequence S2, loop sequence L2 and stem sequence S2. These stem loop sequences are double-stranded between two separate strands and thus do not form stem loop structures. In step B, the Lp1 primer is extended by means of polymerase having strand displacement activity to form a double-stranded/single-stranded DNA hybrid 72 as shown before step C. This hybrid DNA 72 is characterized by the presence of at its 3'-end, a 3'-extendable end formed by stem S2.

In step C, the extendable 3'-end of the DNA hybrid in step B is extended, to form a double stranded DNA 74 as illustrated and displace a single stranded DNA 76. The single-stranded DNA 76 has the sequence from 5'-end to 3'-end of loop L1, stem S1, homology site 1 H1, linking region, homology site 2 H2, and stem loop S2-L2.

In step D, primer P2, a reverse DASL primer, which has a sequence complementary to homology site 2 at the 3'-end and a sequence capable of forming stem loop S2-L2 in its 5'-end, binds to the single stranded DNA 76 in step C.

In step E, bound primer P2 is extended at the 3'-end by means of a polymerase, having strand displacement activity, to form a double stranded DNA 78 with loop L1 sequence, stem S1 sequence, homology site 1 H1, linking region, homology site 2 H2, and followed by two stem-loop structures at the 3'-end.

In step F, the extendable 3'-end is extended by means of a polymerase having strand displacement activity, to form a double stranded DNA 80 as illustrated and a single stranded DNA 82, which has at its 3'-end a loop L1 sequence, a S1 sequence, a target H1 sequence, a linking region, a target H2 sequence and a stem loop S2-L2 at the 5'-end.

In step G, a primer P1 with sequence capable of forming stem loop S1-L1 at its 5'-end and sequence complementary to target homology site 1 H1 at 3'-end, binds to the single-stranded DNA 82 at the H1 homology site 1.

In step H, the bound primer P1 is extended by means of a polymerase with strand displacement activity, to form a double stranded/single-stranded hybrid DNA 84. From the 5'-end, there is the stem loop L1-S1, on one strand, and a single stranded DNA with the loop L1 and stem S1 sequence, followed by double-stranded H1, linking region and H2 sequence, followed by a 3'-end sequence of a stem-loop S2-L2.

In step I, the primer Lp1, with same sequence as in steps A, and B, binds to the double-stranded/single-stranded hybrid 84.

In step J, the bound primer LP1, is extended by means of a polymerase, with displacement activity, to form a double stranded DNA 86 as illustrated and a single-stranded DNA 16 molecule, which can be used to initiate new amplification cycles according to amplification pathways A and B (FIG. 5 and FIG. 6).

By following steps A' through J' and using loop primer Lp2, DASL primers P1 and P2, similar to steps A through J, the other type of DASL single stranded DNA, single-stranded DNA 10 can be generated.

Because loop primers convert some double stranded DNA into a single-stranded DASL DNA, which can be amplified by amplification pathways illustrated in FIGS. 5 and 6, the reaction can be accelerated by these loop primers.

Figure 8:
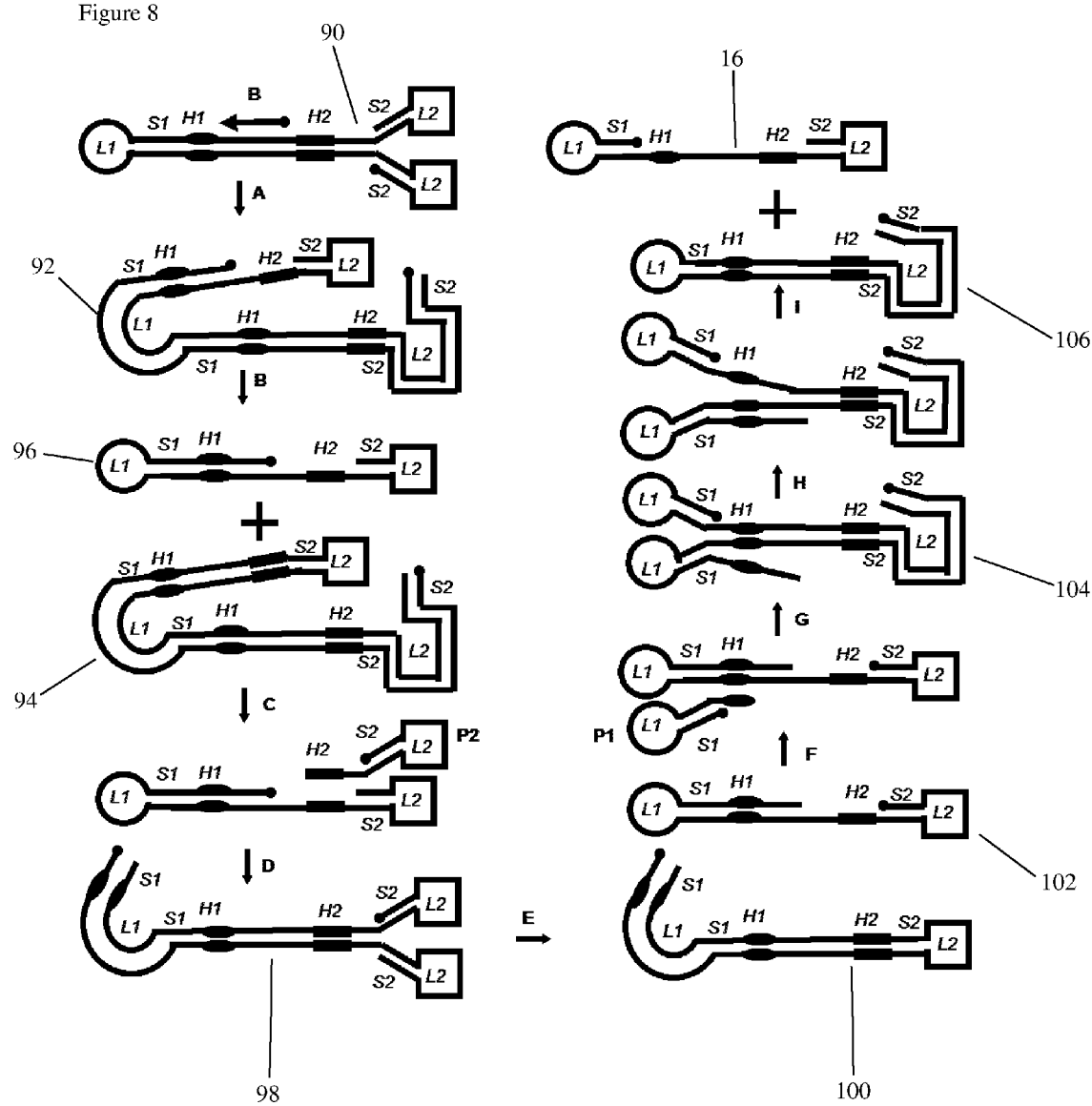
FIG. 8 shows the use of booster primers in a preferred embodiment of the present invention.

Referring to FIG. 8, which illustrate the role of a booster primer in facilitating a DASL amplification processes, starting in step A, a booster primer B binds to a double stranded by-product DNA 90 in the amplification pathway illustrated in FIGS. 5 and 6. This DNA 90 has a loop L1 at the 5'-end, a stem S1, homology site 1 H1, linking region, homology site 2 H2 and two side-by-side stem-loop S2-L2 structures at the 3'-end. Booster primer B binds to the linking region between the H1 and H2 homology sites, to avoid competing for target binding with either the forward DASL primer P1 or reverse DASL primer P2, and to avoid the formation of primer-primer by-products between the booster primer B and either of the two DASL primers P1 and P2. These by-products are undesirable, as they may slow down the target amplification reactions. The bound booster primer B is then extended by means of a polymerase with strand displacement activity, to form a new extension strand, and thus a new double-strand-single-strand hybrid product 92 as illustrated in step A. This structure has a loop L2 with an extendable 3'-end at one of its ends.

In step B, the extendable 3'-end in step A is extended by means of a polymerase with strand displacement activity, to form a double stranded DNA 94 with two joined units of DASL sequence and a double-stranded-single-stranded hybrid DNA 96. This hybrid DNA 96 has a loop L1 at its 5'-end, followed by stem S1, a double-stranded homology site 1 H1, a double-stranded linking region, a single-stranded homology site 2 H2, and a stem-loop structure S2-L2 at the 3'-end.

In step C, a primer P2 with a stem-loop S2-L2 at is 5'-end and a H2 binding sequence at its 3'-end, binds to the single-stranded homology site 2 H2 of the hybrid DNA 96 in step B.

In step D, the bound primer P2 is extended by means of a polymerase with strand displacement activity, to form a double stranded DNA 98 with a double-stranded stem sequence S1 at its 5'-end, double-stranded loop sequence L1, stem sequence S1, homology site 1 H1, linking region, homology site 2 H2 and two side-by-side stem loop S2-L2 structures at the 3'-end.

In step E, the extendable 3'-end of one of the two side-by-side stem loops is extended by means of a polymerase with strand displacement activity, to form a double stranded DNA 100 as illustrated and a double-stranded-single-stranded hybrid DNA 102. This hybrid DNA 102 has a loop L1 at its 3'-end, followed by stem S1, a double-stranded homology site 1 H1, a double-stranded linking region, a single-stranded homology site 2 H2, and a stem-loop structure S2-L2 at the 5'-end.

In step F, a primer P1 with sequence capable of forming stem loop S1-L1 at its 5'-end and sequence complementary to target homology site 1 H1 at 3'-end, binds to the double-stranded H1 region of the hybrid DNA 102 in step E.

In step G, the bound primer P1 is extended by means of a polymerase with strand displacement activity, to form a double-stranded-single-stranded DNA hybrid 104, which starts at the 5'-end with two side-by-side stem-loops L1-S1, followed by a double-stranded homology site 1 H1, linking region, homology site 2 H2, a stem sequence S2, a loop sequence L2 and a stem sequence S2 at the 3'-end. This hybrid DNA 104 also has, beside double-stranded H1 region, in a separate strand, a single-stranded homology site 1 H1.

In step H, in a reversible transformation of the DNA conformation, the strand carrying a single-stranded homology site, binds with one of two strand of the double-stranded H1 region to form an extendable 3'-end, as illustrated.

In step I, the extendable 3'-end is extended by means of a polymerase with strand displacement activity, to form a double stranded DNA 106 as illustrated and a DASL single-stranded DNA 16, which enters amplification pathways A and B for amplification (FIGS. 5 and 6).

By starting with the DNA with structure which is similar to that in step A, that is, another double stranded by-product in amplification the pathway illustrated in FIG. 6, with a loop L2 at the 3'-end, a stem S2, homology site 2 H2, linking region, homology site 1 H1 and two stem-loop S1-L1 structures at the 5'-end, and following steps parallel to steps A to I, another single-stranded DNA, single-stranded DNA 10 (see FIG. 3), can be generated.

Because booster primers can produce the DASL single-stranded DNA 10 and single-stranded DNA 16, from some related double-stranded products during amplification, booster primers can speed up the amplification process.

Primer Design and Uses

When designing a primer according to this invention, sufficient sequence in length, i.e., number of bases, and composition, i.e., GC content, and melting temperature, are preferably chosen to ensure specific and efficient binding of the primer to the template (Kampke et al., *Bioinformatics* 17:214-225 (2001)). Generally, primers suitable for use in DASL are more than 10 nucleotides and fewer than 70 nucleotides in length. A primer may have a GC content around 50%, preferably between 30-70%, more preferably between 40-60%. The melting temperature of a primer is determined by the length and GC content of that primer. Preferably the melting temperature Tm of a primer is close to the temperature at which the binding and amplification will take place, from 5° C. below to about 15° C. above the reaction temperature, preferably from 2° C. below to about 5° C. above the reaction temperature. If the temperature of the binding and amplification is 60° C., the melting temperature of a pair of primers designed for that reaction may be in a range between 55° C. and 70° C. and more preferably 58-65° C. In addition, primers should not have un-intended secondary structures, such as un-intended stem loops or hairpins and un-intended primer-primer by-products "primer-dimers". Estimation of Tm and prediction of secondary structures for a primer sequence may be assisted by some software such as Mfold (M. Zuker. Mfold web server for nucleic acid folding and hybridization prediction. Nucleic Acids Res. 31 (13), 3406-3415, 2003). Those skilled in the art know that the Tm estimation should take into consideration the reaction conditions, including the primer concentration, magnesium concentration, dNTP and salt concentrations. More information regarding primer design is described by Kampke et al., *Bioinformatics* 17:214-225 (2001). To choose the best primers for a DASL reaction, a set of primers with various sequence and melting temperatures can be experimentally tested in a parallel DASL assay. Primers as described herein can be prepared by synthesis methods well known in the art (see, for example U.S. Pat.

No. 6,214,587). Primers are readily available commercially as custom-made oligonucleotides.

For the DASL primers, such as the primer P1 in FIG. 1, the target binding portion is designed to bind, on its own, to a homology site of a target strand under the DASL reaction conditions. For example, the target binding portion of a DASL primer may have a Tm of around 60° C., preferably 53-70° C. more preferably 57-63° C. A DASL primer preferably contains at least 1-2 guanosine (G) or cytidine (C) bases out of the four bases at the 3'-end to ensure sufficient ability of the primer to bind to target selectively. The base pairings formed by G and C have higher stability than those formed by A and T bases. On the other hand, having more than 2-3 bases of G or C is preferably be avoided at the 3' end of primers, as these primers are more prone to mis-prime or to form primer-dimers.

Preferably, the distance in sequence between the target homology site that a DASL forward primer binds to and the target homology site that a DASL reverse primer binds to should be chosen as short as possible so that the size of the full length amplified DNA product, is as small as possible, in order to minimize the total number of nucleotide bases that needs to be synthesized and thus to shorten overall amplification time. For example, the size of the monomer product for prothrombin gene fragment A in Example 1 (FIG. 9) was 38 bp excluding the stem-loop regions of the construct.

The stem loop portion of a DASL primer can have the following sequence regions, a) a 5'-end stem sequence, b) a loop sequence and c) a sequence that is the reverse complement of the stem ("r-c stem sequence"). Such an array of sequence regions should be ensured to form a stem loop structure under the isothermal reaction conditions. The design can be verified by using a nucleotide sequence secondary structure prediction algorithm. The stem may be 3 to 30 bases in length, preferably 4 to 25 bases, with a GC content of at least 30% and the loop may be 5-30 bases in length. The loop is preferably 10 to 25 bases in length, more preferably 13-20 bases in length. In order to facilitate the formation of the designed stem loop structure in the stem loop primers for efficient and fast reactions, it is preferred that the loop is low in GC content, such as 30-50% GC or lower. This helps to encourage stem loop structure formation and discourage inter-strand base pairing in stem loop regions of DNA templates, such as between the top and bottom (forward or reverse DNA strands). It is also preferred that the loop has a low tendency for forming alternative intra-loop structures, by designing the loop with only pyrimidine bases or only purine bases. For example, a loop can be formed by C, or A bases, as C and A do not form strong Watson Crick base pairings with each other. As another example, poly A loops or poly C loops or poly T loops or poly G loops do not offer intra-loop base pairing.

The loop size can be optimized to increase the rate of amplification reaction. The smaller the loop, such as 3-7 bases in a loop, the faster a loop is formed—a rate that can be referred to as on-rate. The larger the loop, such as more than 30 bases, the slower a loop is formed. For an optimal DASL reaction, for example between 8-30 base pairs, preferably between 10-30 base pairs, more preferably between 13-20 base pairs. An optimal loop size can be determined by designing several primers with the same target binding sequence and the same stem sequence with variable loop sizes.

For a given loop size, the stem length and sequence can also be adjusted. In general, the longer the stem sequence or the higher GC content of a stem, the slower a pre-formed stem loop may be opened. In other words, the stem sequence and base composition may affect the opening rate, or the off-rate. For an optimal DASL reaction with an optimal off-rate, a stem should have preferably 4-25 base pairs, or preferably 4-15 base pairs, or preferably between 4-8 bases. An optimal stem length and base composition can be determined by designing several primers with a) the same target binding sequence, b) the same loop sequence and c) variable stem sequence length and/or base composition.

As described above, the stem loop primers can be preferably designed for more efficient amplification of nucleic acid targets by adjusting the size of the stem in the stem loop, the size of the loop in the stem loop and the base content of the loop in the stem loop. More specifically, a stem loop primer may assume an overall relatively short primer sequence length so that the design stem loop primers are efficient in quickly binding to template during DASL reactions. For example, an efficient stem loop primer for a DASL reaction may include 16 base loop sequence, a stem sequence of 6 bases, a r-c stem sequence of 6 bases, a target binding sequence of 20 bases, with an overall primer length of 48 bases.

In general, it is preferred that a stem loop primer has a total length of 30-75 bases, more preferably 40-60 bases. In order to shorten the total length of the primer, the 5' portion of the target binding region can serve both as part of a loop and/or a r-c stem. Alternatively, the 5' portion of the target binding region can serve as part or the entirety of a r-c stem. For example, in this stem loop primer, the target binding region overlaps with the loop and r-c stem:

```
cagggca aaa aaa aaa aaa aaGTA TGCCCG GTAAACAG
(stem)  (loop)(r-c stem)
        (TARGET BINDING REGION)
```

In the target binding sequence (in capital letters), "GTA" serves as a part of a loop and "TGCCCG" serves a r-c stem. In order to have a desirable loop size of 10-30 bases (17 bases in this example), 14 A's preceded "GTA" as the rest of loop. The stem sequence "cgggca" preceded the loop sequence ensures the formation of stem loop structure. Note: the underlined are the stem and r-c stem regions. In some alternative embodiments, the loop and/or r-c stem may overlap into the target binding sequence by as much as 90% of the target binding sequence.

The sequence of the r-c stem is substantially or perfectly that of the reverse complement of the stem structure. The stem loop structure may have a melting temperature Tm close to or 5-20° C. greater than the reaction temperature. For example, for a reaction at 60° C., the Tm of the stem loop may be 60-80° C., preferably 65-75° C. In order to minimize the number of bases in the stem and r-c stem regions, a high GC-content can be used, up to 100% GC content. In other words, all the bases in these two regions can be G or C. The Tm of a stem-loop structure can be predicted by an algorithm and software program such as the Mfold (M. Zuker. Mfold web server for nucleic acid folding and hybridization prediction. Nucleic Acids Res. 31 (13), 3406-3415, 2003). Such prediction algorithms are useful in predicting not only that the intended stem-loop will be formed under the defined reaction conditions, such as the intended magnesium concentration and ionic strength, but also that alternative secondary structures are avoided or minimized. If any alternative secondary structures are found, new designs of stem loop structures, for example, by altering the stem and corresponding r-c stem sequence, or loop sequence, may be examined to ensure that the intended stem loop structure is formed and alternative secondary structures are avoided/or destabilized based on thermodynamic parameters, such as free energy change or the melting temperature. For example, alternative structures should have Tm values that are substantially lower than that for the intended stem loop structure. Methods of examining secondary structures of nucleic acid are well known to those skilled in the art, for example the Mfold (M. Zuker. Mfold web server for nucleic acid folding and hybridization prediction. Nucleic Acids Res. 31 (13), 3406-3415, 2003).

By default, the forward and reverse DASL primers may have different loop structures, different stems, or otherwise different stem loop structures, from each other. Alternatively, the forward and reverse DASL primers may share the same stem loop sequence and thus structure. In other words, such as the L1-S1 for the forward DASL primer, and the L2-S2 for the reverse DASL primer, may be of the same sequence.

The displacement primers, such as the D1 and D2 primers in FIG. 4, should be designed to ensure that they bind to the targets under the DASL reaction conditions using the primer design considerations outlined above. The forward displacement primers should be designed just upstream, preferably, 1-100 base pairs upstream, more preferably 1-50 base pairs upstream, of a forward DASL primer. The reverse displacement primers should be designed just downstream, preferably, 1-100 base pairs downstream, more preferably 1-50 base pairs downstream, of a reverse DASL primer. The Tm of a displacement primer may have be close to the reaction temperature. For example, for DASL reaction at 60° C., Tm for the displacement primer may be around 60° C., preferably 53-70° C., more preferably 57-63° C.

Loop primers, such as the Lp1 and Lp2 primers in FIG. 7, can be designed to bind to a part or the entire loop region of a DASL product. By "a part", it is meant that at least five bases in sequence of the loop region. At the 3'-end, the loop primer may adopt part or the entire sequence of a loop sequence of a DASL primer. The loop primer may contain at its 5'-end, sequence to the stem region. Alternatively, other structures such as a stem loop can be attached to the 5'-end of the primer. The loop primer may have a Tm close to the reaction temperature. For example, for a DASL reaction at 60° C., Tm of a loop primer may be around 60° C., preferably 53-70° C., more preferably 57-63° C. The loop primer sequence may be chosen such that the strandedness is the same as the loop sequence of the DASL primers. In other words, the loop primer sequence may be derived from the loop sequence, not the reverse complement, of a DASL primer. This is to avoid loop primers binding to the DASL primers to cause extension reaction between primers without the involvement of target DNA.

A method of exponentially and selectively amplifying a nucleic acid target is provided, where part or the entirety of the stem loops for the two DASL primers of the template share the same sequence and a single loop primer with the shared sequence are used in a DASL amplification reaction.

Booster primers, such as the primer B in FIG. 8, can be designed to bind to part or the entirety of the linking region linking between homology site 1 and homology site 2 of target DNA (see for example FIG. 3, FIG. 4 and FIG. 8). By "a part", it is meant that at least five bases in sequence of the linking region. This linking region is preferably 3-50 base pairs long. The length of this region is preferably long enough to allow the design of a booster primer, and short enough to amplify as short a product as possible. In Example 1, a stretch of 5 base pairs was included as the linking region, allowing 35 base pairs for a monomer product excluding stem loops (107 by including stem loops) was amplified. Short products can be more quickly amplified than longer products. In order to amplify a relatively short product, at the 5'-end of a booster primer, the sequence of the primer can overlap with either the homology site 1 or the homology site 2, depending on the orientation of the booster primer. Whenever a booster overlaps with other primers, such as a DASL primer or another booster primer, such an overlap is between sequences of primers of the same strandedness. For example, the 3'-end of a forward DASL primer and the 5'-end of a forward booster primer can overlap with each other. For example, note the experiment in Example 1 where the booster primer overlapped with the forward DASL primer to minimize the size the monomer product. It is preferred that the 3'-end of a booster primers are not overlapped with the 3'-end of a DASL primer. If the 3'-ends of the primers overlap, extension and reaction between primers without the involvement of target DNA can interfere with the amplification of target DNA. In addition, when a booster primer is to overlap with the homology binding sequence of DASL primers, it is preferred such an overlap is only partial, that is only for less than 50% of the homology site of the DASL primer, and 50% of the booster primer's template binding sequence, to avoid/minimize competition for binding with template between the DASL primer and the booster primer.

More than one booster primer, such as two or more booster primers, can be used. For example, multiple non-overlapping booster primers can be used, with individual primers binding either forward or reverse template strands. For example, booster primers 1 and 2 both bind to forward template strand, or reverse template strand. Alternatively booster primer 1 may bind to the forward strand and booster primer 2 may bind to the reverse strand, or vice versa. In the latter case, booster primers can face each other head to head (3'-end to 3'-end) or back to back (5'-end to 5'-end). When overlapping booster primers are to be used, it is preferred that the overlaps are between 5' end of one primer and 3'-end of another primer, or between 5'ends of primers. Overlaps between 3'-ends of booster primers should be avoided to avoid/minimize competition between primer-primer reaction and the template dependent amplification reactions.

Only a pair of DASL primers, one for the forward direction and another for the reverse direction, surrounding the target region to be amplified, may preferably be used, as in Example 6.

In addition to the DASL primers, at least one type of primer from the following list of types of primers may be included to increase the rate of DASL reaction, and/or to increase the yield of products, specificity and/or sensitivity of the reaction: a) displacement primers, b) booster primers and/or c) loop primers. Preferably, at least two types of primers from this list are included with DASL primers in a DASL reaction. For example, a DASL reaction includes the forward and reverse DASL primers, displacement primers, and booster primers, in the presence of a polymerase with displacement activity in the appropriate buffer and other temperature conditions. Alternatively, a DASL reaction includes the forward and reverse DASL primers, displacement primers, and loop primers, in the presence of a polymerase with displacement activity in the appropriate buffer and other temperature conditions. In one preferred embodiment, a DASL reaction includes all three types of additional primers: the forward and reverse DASL primers, forward and reverse displacement primers, booster primers and loop primers, in the presence of a polymerase with displacement activity in the appropriate buffer and other temperature conditions such as in Examples 1 to 5.

Concentrations of primers in a DASL reaction can be optimized to ensure that the DASL reaction proceeds quickly and efficiently. For example, where multiple types of primers are used, the two DASL primers have the highest concentrations, followed by the booster primers and loop primers in the intermediate concentrations, and the displacement primers having the lowest concentrations to direct the reactions towards optimized rate of DASL reactions and minimized background reactions. Preferably, each of the booster primers and loop primers has 0.3-0.7× the concentration of a DASL primer and each of the displacement primer has 0.05 to 0.2× of the concentration of a DASL primer. For example, the DASL primers may each have around 2 µM in concentration, each of booster primer(s) and loop primer(s) may have around 1 µM in concentration, and each of the displacement primers may have around 0.2 µM in concentration. As another example, the DASL primers may each be around 1 µM in concentration, each of booster primer(s) and loop primer(s) may be around 0.6 µM, and each of the displacement primers may be around 0.15 µM in concentration. In addition, rates of DNA extension reactions, including DASL isothermal amplification reactions, can be modulated by changing overall primer concentration. Under some conditions, an increase in primer concentration in DASL primers from 2 µM to 3 µM, can lead to increase in the reaction rate. However, too high overall primer concentration can lead to reduced specificity due to primer-primer dimer or other by-products. The optimal concentrations of primers can be tested in a series of parallel DASL reactions where overall and/or individual primer concentrations are varied and resulting products are analyzed for yield, reaction time and the presence of desired products, for example by agarose gel electrophoresis, see Examples 1 to 6.

Preferably, multiple sets of DASL primers can be utilized in a single DASL reaction vessel for simultaneously amplifying multiple amplicons, such amplification reactions are referred to as multiplex amplification reactions. The term "amplicon" is used here to refer to a target or target region to be amplified. Those skilled in the art know that multiplex amplification reactions can be optimized for the desired outcome, for example, a similar level of amplification for all amplicons in a multiplex reaction. Alternatively, preferential amplification of some amplicons, for example, small amplicons, can also be achieved. Reaction conditions such as primer concentration for each amplicon, reaction time, pH, magnesium concentration, enzyme concentration can be varied to achieve the desired multiplex amplification outcomes. Two amplicons can be amplified in a DASL reaction vessel. Such a reaction is often referred to as 2-plex. More than 2 amplicons can also be multiplexed. For example, in a 3-plex reaction, three different regions of a virus can be amplified in the same tube. As another example of multiplex amplification using DASL, in a genotyping assay, 4 or more, or even 10 or more amplicons may be amplified for the purpose of interrogating the sequences at various sequence loci. Multiplexing is commonly used in Single Nucleotide Polymorphism (SNP) analysis and in detecting pathogens (Jessing et al., J. Clin. Microbiol. 41:4095-4100 (2003)). In optimizing a multiplex DASL method, the primer concentrations may be optimized first. Preferably, the total concentrations of primers in a multiplex DASL reaction for a particular primer type, for example, DASL primers, loop primers, booster primers or flanking displacement primers, remain close to those for an optimized single-amplicon reaction. In addition, multiple amplicon amplification can share loop primer(s). For example, DASL primers for targets 1, 2 and 3 can share the same loop sequence and thus a single loop primer can be used for the entire multiplex reaction amplifying targets 1, 2 and 3 simultaneously.

Polymerases

Polymerases are selected for DASL on the basis of their DNA polymerization and strand displacement activity at the desired temperature range. It is possible to have two separate enzymes, one as polymerase, and one that provides strand displacement activity. In a preferred embodiment, one enzyme possesses both activities. For example, Bst DNA polymerase large fragment can be used to provide both polymerase and strand displacement activities.

The DNA polymerase with strand displacement activities can be selected from a group of polymerases lacking 5' to 3' exonuclease activity and which may optionally lack 3'-5' exonuclease activity.

Examples of suitable DNA polymerases include large fragment of Bst DNA polymerase and large fragment of Bst 2.0 DNA polymerase (New England Biolabs, Inc., Beverly, Mass.), an exonuclease-deficient Klenow fragment of E. coli DNA polymerase I (New England Biolabs, Inc., Beverly, Mass.), an exonuclease deficient T7 DNA polymerase (Sequenase; USB, Cleveland, Ohio), Klenow fragment of E. coli DNA polymerase I (New England Biolabs, Inc., Beverly, Mass.), KlenTaq DNA polymerase (AB Peptides, St Louis, Mo.), T5 DNA polymerase (U.S. Pat. No. 5,716,819), and Pol III DNA polymerase (U.S. Pat. No. 6,555,349), Bca(exo-) DNA polymerase, Vent(Exo-) DNA polymerase (exonuclease activity-free Vent DNA polymerase), Deep-Vent DNA polymerase, DeepVent(Exo-) DNA polymerase (exonuclease activity-free DeepVent DNA polymerase), Φ29 phage DNA polymerase, MS-2 phage DNA polymerase, Z-Taq DNA polymerase' (Takara Shuzo), KOD DNA polymerase (TOYOBO). Preferably, DNA polymerases possessing strand-displacement activity, such as Bst DNA polymerase large fragment, the exonuclease-deficient Klenow fragment of E. coli DNA polymerase I, and Sequenase, are used for DASL amplification. Bst DNA polymerase, Bca(exo-) DNA polymerase and similar enzymes are preferred because they are each having both polymerization and strand displacement activities and with thermal stability to a certain degree and high catalytic activity at the high temperatures between 55-70° C. For Bst 2.0 DNA polymerase (New England Biolabs, Ipswich, Mass., USA), for example, a temperature of 60-69° C. can be used. In addition, various mutants of these enzymes can be used, so long as they have suitable activity of sequence-dependent complementary strand extension and the strand displacing activity. Such mutants include truncated enzymes having only the structures with catalytic activity or mutant enzymes whose catalytic activity, stability, or thermal stability has been modified by amino acid mutations.

Binding Primers to Nucleic Acid Templates and Conducting DNA Extension

Conditions of binding primer to nucleic acid templates are well-described and known to those skilled in the art, as described in "Molecular Cloning and Laboratory Manual" $2^{nd}$ ed. Sambrook, Rich and Maniatis, pub. Cold Spring Harbor (2003). In a method for enzymatically extending DNA of the present invention, a reaction comprising a series of steps is carried out in the presence of a buffer giving a suitable pH, salt concentration required for primer binding and maintaining the catalytic activity of the enzyme, preservatives for the enzyme, and in addition if needed, a Tm regulator etc. The buffer with a buffering action in a range from neutral to weak alkaline pH, such as from pH 6.5-10, may be used. The pH is adjusted depending on the type of DNA polymerase used. Examples of salts to be added to maintain the enzyme activity and to modify the Tm of the polynucleotide include KCl, NaCl, MgCl2, MgSO4, (NH4)2SO4, etc. Enzyme preservatives include bovine serum albumin and sugars. Preferably, buffers optimized for a polymerase with strand displacement activity are used. For example, the buffer from the supplier of the enzyme Bst 2.0 DNA polymerase (large fragment) (New England Biolabs, Ipswich, Mass., USA), that is, 20 mM Tris-HCl, 10 mM (NH4)2SO4, 50 mM KCl, 2 mM MgSO4, 0.1% Tween® 20, pH 8.8), or an equivalent buffer, may be used to conduct the DASL reaction.

A primer can bind to a single stranded nucleic acid more easily than to a strand already in the form of a double stranded DNA. When a double-stranded DNA is used as a template, the DNA needs to be converted to single strands by denaturation prior to the primer binding, in a polymerase chain reaction. In a DASL reaction of complementary strand extension using double stranded DNA template, double stranded DNA can be destabilized by a Tm regulator such as betaine and other buffer and reaction conditions. Such destabilization is sufficient to allow a primer to transiently bind to a template and primer extension to occur instantaneously upon primer binding, without completely converting the double stranded structure into single strands.

An initial high temperature denaturation step to generate initial single-stranded template may be used to speed up DASL reactions. For example, a method of exponentially and selectively amplifying a nucleic acid target according to a preferred embodiment of the invention is provided, wherein the target DNA is pre-heated at 70° C. or higher, preferably 90-100° C. for 30 seconds or longer, in the presence or absence of primers, before the polymerase with strand displacement activity and reaction buffer are added. Pre-denaturing the template is expected to increase the proportion of templates bound with primers at the beginning of a DASL reaction.

Alternatively, an optional alkaline denaturation step can be added to denature the template at the beginning of a reaction. Such an alkaline condition can be created by adding sodium hydroxide to 5-20 mM. In one aspect of the invention, low concentration of the alkali is used such as 2-10 mM, such low concentrations of alkali can be conveniently neutralized after alkaline denaturation by a reaction buffer added in a DASL reaction, e.g., 20 mM Tris in the Bst 2.0 DNA polymerase (large fragment) buffer cited above. In this way, a DASL reaction can occur immediately following denaturation. In either the heat denaturation or alkaline denaturation, all the required primers, e.g., the DASL primers, displacement primers, loop primers and/or booster primers can be included in the same mixture as the template and denatured at the same time. In this way, as the mixture is cooled or neutralized, the primers can bind the single-stranded template immediately prior to a DASL reaction. As the enzyme and dNTPs may be heat- and alkali-labile, the temperature denaturation should exclude these components of reaction.

Melting temperature (Tm) regulators lower the Tm of template DNA, including the Tm for strand-to-strand association between strands of templates and intermediate products. These Tm regulators include betaine (N,N,N-trimethylglycine), proline, dimethylsulfoxide (DMSO), formamide, and trimethylamine N-oxide. Similarly, propanediol is another molecular crowding reagent (Zhang et al., BioTechniques, Vol. 47, pp. 775-779 (2009)) suitable for the reactions according to this invention. When a Tm regulator is used, binding of the above-mentioned primer can be regulated within a relatively narrow temperature range, such as a 20° C. range. Moreover, betaine and tetraalkylammonium salts effectively contribute to the improvement of the efficiency of strand displacement due to their melting and stabilizing action. The addition of betaine at a concentration of about 0.2 to 3.0 M, preferably about 0.5 to 1.5 M to the reaction solution is expected to enhance the amplification of DNAs in preferred embodiments of the present invention. Polyethylene glycol (PEG) has been used to create an artificial molecular crowding condition by excluding water and creating electrostatic interaction with solute polycations (Miyoshi, et al., *Biochemistry* 41:15017-15024 (2002)). When PEG (7.5%) is added to a DNA ligation reaction, the reaction time is reduced to 5 min (Quick Ligation Kit, New England Biolabs, Inc. (Beverly, Mass.)). PEG has also been added into helicase unwinding assays to increase the efficiency of the reaction (Dong, et al., *Proc. Natl. Acad. Sci. USA* 93:14456-14461 (1996)). PEG or other molecular crowding reagents may also increase the effective concentrations of enzymes and nucleic acids in DASL reaction and thus reduce the reaction time and the enzyme concentration needed for the reaction.

Suitable temperature conditions for enzyme reactions can be readily chosen based on Tm of primer to template association and the acceptable temperature range for the polymerase, for example, 58-70° C. is a range suitable for Bst DNA polymerase-based enzymes. The amount of a Tm regulator can be adjusted to increase or decrease the effective Tm of a primer binding to template. Those skilled in the art can readily choose proper reaction temperature, depending on the primer nucleotide sequence, Tm and the amount of Tm regulator and a compatible polymerase with strand displacement activity. An optimal temperature for a given set of primers and reaction conditions can also be determined experimentally in a series of parallel assays by varying the temperature of the reaction mixture and comparing amplification products using agarose gel electrophoresis.

The same conditions for binding primers to templates mentioned can be considered for ensuring the extension within the template DNA, such as the within-template 3'-end extension (for example, see step D of FIG. 1) or template to template interaction or template transition between states (for example, see step A6, FIG. 3), and strand displacement.

Template DNA suitable for the methods according to this invention can be prepared in various methods, for example they can be isolated from tissues, blood and other biological fluids or cultured cells using appropriate DNA isolation methods. These methods are well-described for example in Maniatis T, Fritsch E F, Sambrook J (1982) Molecular cloning: A laboratory manual, Cold Spring Harbor Laboratory, Cold Spring Harbor, N.Y.). Methods and kits for DNA isolation are also widely available commercially. DNA may not need to be isolated from contaminants present in specimens such as tissues, blood and other biological fluids prior to use in the DASL methods according to this invention. Template DNA can also be synthetically (chemically) made.

An amplification reaction can be in a volume scale of nanoliters to several milliliters. In some methods of performing screening assays using ultra-low volumes, nanoliter scale of solutions can be transferred into small reaction vessels such as the wells in 96-, 384-, 1536-well microplates. The DASL reaction can be set up by pipetting and mixing nanoliters of polymerase, reaction buffer, primers and other reagents and samples or the mixtures of these reagents and samples together into the reaction vessels. Such reactions can be incubated to the desired reaction temperature range, for example, 30-70° C., in order to increase the sensitivity by sampling a large volume of a sample, the volume of a reaction can be scaled up from those in Examples 1-6, to hundreds of microliters to several milliliters. It is preferred that the concentrations of the reagents are maintained relative to those in Examples 1-6 or discussed in the specification. Those skilled in the art can easily optimize the concentrations of the reagents and conditions of reactions in these large volumes.

RNA Detection

Prior to amplification, RNA can be converted to single-stranded cDNA, by using appropriate reverse transcriptase and a suitable primer or mixture of primers. After the cDNAs are obtained, they can be amplified using the methods described above, because the DASL methods including the methods of generation of single-stranded DNA 10 and single-stranded DNA 16, work on double-stranded and single-stranded target DNA or DNA-RNA hybrid double-stranded DNA. In the latter case, only the DNA strand of the hybrid will act as template for DASL amplification. Various reverse transcriptases are readily commercially available. The primers for cDNA extension can be a target specific primer or random sequence primers, or a primer with poly A bases. Such primers and methods of use in reverse transcription are widely provided from suppliers when the reverse transcriptase is purchased, or otherwise widely described, for example in this reference—Maniatis T, Fritsch E F, Sambrook J (1982) Molecular cloning: A laboratory manual, Cold Spring Harbor Laboratory, Cold Spring Harbor, N.Y.).

Messenger RNA, often abbreviated as mRNA, as well as total RNA containing mRNA, can be isolated from various biological sources. Template RNA suitable for the methods according to this invention can be prepared in various methods, for example they can be isolated from tissues, blood and other biological fluids or cell lines using appropriate DNA isolation methods. These methods are well-described for example in Maniatis T, Fritsch E F, Sambrook J (1982) Molecular cloning: A laboratory manual, Cold Spring Harbor Laboratory, Cold Spring Harbor, N.Y. Methods and kits for RNA isolation are also widely available commercially. Template RNA containing specimens such as tissues, blood and other biological fluids may not need to be isolated from such sources prior to use in the DASL methods according to this invention.

A reverse transcriptase suitable for use includes any commercially available enzyme used for reverse transcriptase such as M-MuLV, Avian Myeloblastosis Virus (AMV) reverse transcriptase. When the reverse transcriptase is thermolabile, the reaction can be incubated first at a low temperature, for example 37 to 42° C. or a similar temperature, for reverse transcription, followed by a high temperature incubation for isothermal amplification by DASL for example at 63° C. Where two different buffer systems are used for RT-DASL, one for RT and the other for the amplification step, the first strand cDNA is extended by a reverse transcriptase in the presence of either an oligo-dT primer or a sequence-specific primer complimentary or a random primer to the target RNA sequence. In an aspect of the invention, the RT buffer and composition in a two-stage method is 50 mM Tris-HCl, pH 8.3, 75 mM KCl, 3 mM $MgCl_2$, 10 mM DTT. AMV, 50 mM Tris acetate, pH 8.4, 75 mM potassium acetate, 8 mM magnesium acetate, 10 mM DTT, dNTPs, and target RNA. Aliquots of cDNA copies from the reverse transcription reaction are then transferred into a second reaction buffer and are subsequently amplified in the presence of a polymerase in a DASL reaction.

RNA may be amplified by two consecutive reactions, reverse transcription and a DASL DNA amplification reaction. Both reactions occur in a common reaction vessel using a common buffer for both the reverse transcription and the DASL reaction. After sample and all reagents including the RNA, reverse transcription primers, and reverse transcriptase, and DASL primers and a polymerase with displacement activity are added, the reaction vessel is included at a low temperature around 37° C. first for reverse transcription, followed by a DASL reaction at a high temperature at around 60° C. The benefit of such a combined single-tube reaction is to save time and provide convenience to the operator.

The reverse transcription and the DASL reactions may be conducted further, at a single reaction temperature, by using a thermostable reverse transcriptase (U.S. Pat. No. 5,322,770) such as (SuperScript™, ThermoScript™ (Invitrogen, Carlsbad, Calif.), or Transcriptor (Roche, Basel, Switzerland) reverse transcriptase or a polymerase with reverse transcriptase activity such as Tth polymerase ThermoScript™ (Invitrogen, Carlsbad, Calif.)). In such system, cDNA copies are generated and amplified from a RNA target concurrently using a reverse transcriptase, and a DNA polymerase and a common buffer system and in an integrated incubation step. The first strand cDNA is first extended by a reverse transcriptase. The RNA-DNA duplex from the reverse transcription reaction is partially unwound by the reaction system. In an aspect of the invention, after the full length of the RNA/cDNA duplex is unwound, the single-stranded RNA enters a next round of reverse transcription reaction generating more first strand cDNA. The cDNA is subjected to amplification in the DASL reaction. This process repeats itself to achieve exponential amplification of DNA which originates from the RNA target sequence.

Detection of Amplified Nucleic Acids

DASL reactions involving primer binding and DNA extension typically take place for a few minutes to an hour. In order to shorten the time duration of reaction and improve reaction yield, various conditions can be examined experimentally, including reaction temperature, primer concentration, DASL primer, concentration ratios of displacement primer, booster primer and/or loop primer, magnesium concentration, dNTP concentration, enzyme concentration, template concentration etc. Preferably, the reaction may proceed to a high level of DNA product, or a plateau level, beyond which further incubation of the reaction does not significantly increase the quantity of products. Nonetheless, for some methods of detecting amplified products, such as using a fluorescent dye like EvaGreen or Sybr Green to monitor the fluorescence of amplified DNA, the reaction only needs to accumulate sufficient quantity to exceed the detection threshold such as the Cq or Ct (threshold cycle or threshold time) of a fluorescent detector of a real-time PCR machine.

Amplified nucleic acid products may be detected by various methods. Preferably, a fluorescent intercalator like ethidium bromide, which emits fluorescence by reacting with double-stranded DNA, is used to detect amplified DNA. Ethidium bromide can be used to stain the solution of the completed reaction. A positive amplification reaction can elicit ethidium bromide fluorescence differently from that of a negative reaction. When the nucleic acids are present in the amplified products in high levels, ethidium bromide staining can be used to visually inspect or inspect with an aid of a UV transilluminator. PicoGreen™ (Tomlinson et al., Appl Environ Microbiol 73:4040-4047(2007)), Sybr Green I (Iwamoto et al., J Clin Microbiol 41:2616-2622(2003)), EvaGreen (Qiao et al. Biotechnol Lett, 29:1939-1946(2007)), GelRed (Nakao et al. BMC Microbiology 10:296 (2010)), can be used instead of ethidium bromide to directly stain solutions of a completed amplification reaction. Alternatively, turbidity can be used to detect the presence of amplified nucleic acids (Mori et al., Biochem Biophys Res Commun 289:150-154 (2001)). The solution staining followed by a visual inspection is appealing for applications such as point of care diagnostics, because it takes very little time to obtain a qualitative result, following the amplification of nucleic acid in testing samples. Hydroxy naphthol blue can also be used to stain and detect amplified DNA. A dye such as hydroxy naphthol blue, can be added prior to a DASL reaction as the dye does not inhibit isothermal amplification reactions in a suitable concentration range (such as around 120 µM).

In a preferred embodiment, a fluorescent dye such as Sybr Green or EvaGreen can be included in the reaction and the reaction is monitored in real-time by monitoring the fluorescence produced as the DASL reaction accumulates amplified DNA by a fluorometer or a detector of a real-time PCR machine, at a temperature in the range of about 20° C.-75° C., for example in a range between 60° C.-65° C.

Amplified nucleic acids can also be analyzed by gel electrophoresis followed by ethidium bromide or Sybr® Safe, or Gel Red staining of the gel to visualize bands of amplified DNA (see Examples 1-6).

To assist in detection, primers, and/or the products derived from the primers can be bound to a solid phase. For example, a part of the primer may be labeled with a binding ligand such as biotin. This label subsequently enables the resulting DNA product to be immobilized indirectly via a binding partner such as immobilized avidin or streptavidin, which may be immobilized such as by a magnetic bead or a solid surface. The immobilization of amplified products may thus facilitate its separation from the solution phase, for example from the enzymes, buffers and un-reacted primers and target DNA. The separated product can be detected by a nucleic acid-specific indicator or by binding with a labeling probe. The target nucleic acid fragments can also be recovered by digesting the product with a restriction enzyme which specific recognition sequence may be built in the primer. Alternatively, the label attached to a primer can be a signal moiety such as a fluorescent tag, a radioactive isotope, or another signal provider. Examples of such tags include fluorescent tags such as amine reactive fluorescein ester of carboxyfluorescein-Glen Research, Sterling, Va. Such a primer is preferably a booster primer, a loop primer, or a DASL primer. For example, primers may have tag sequences at the 5' end which are non-complementary to the target nucleotide sequence(s). Such tag sequences may be bound with detection probes in for example a lateral flow membrane of a lateral flow assay device. Such methods of using probes to detect amplified DNA are well-known to those skilled in the art (such as U.S. Pat. No. 8,445,291).

The methods disclosed here can be used to detect the presence or absence of pathogens, genotypes and other targets in samples. When there are targets in samples, amplification can occur using the methods according to this invention. Such amplification can be detected using various detection methods, some of which are discussed here. A result whether such detection is made, in other words, positive or negative, indicates whether or not a target is present or not in the sample. Thus, the amplification methods according to this invention can be used to prepare a diagnostic method and kit.

Also provided is a compact portable device for field use, such as in point-of-care health care settings, using a later flow strip device to detect the amplified nucleic acid. Following nucleic acid amplification, the amplified DNA is applied to the sample area of such a device. As the amplified DNA interacts with probes and capture reagents, a captured line of signal may form to indicate the presence of the amplified DNA. Various methods of detecting amplified DNA, for example, using lateral flow membranes, have been readily available (for example in Lateral flow devices U.S. Pat. No. 7,799,554) to those skilled in the art.

The materials described above, such as a polymerase with strand displacement activity and primers, reaction buffer, as well as other materials can be packaged together in any suitable combination along with instruction on performing preferred methods, as a kit useful for performing, or aiding in the performance of the disclosed methods. It is useful if the kit components in a given kit are designed and adapted for use together in the disclosed method. For example disclosed are kits for amplifying a target nucleic acid in a DASL reaction, the kit comprising one or more reagent compositions and one or more components or reagents for amplification and detection of target nucleic acids. For example, the kits can include one or more reagent compositions and one or more oligonucleotide probes, one or more fluorescent dyes or combination. Another form of kit can comprise a plurality of reagent compositions. The kits also can contain, for example, dNTP nucleotides, buffers, polymerase with strand displacement activity, Tm regulators, magnesium or a combination.

Because the DASL methods are fast, sensitive and robust without requiring a thermal cycler, various industrial applications requiring nucleic acid amplifications are possible. For example, such applications include the diagnosis of human diseases such as infectious diseases and cancer, or methods of genotyping to assist in optimizing therapeutic treatments of patients, and detection of pathogens in food in food surveillance and safety testing where pathogens such as *salmonella, listeria* and *E coli*, which are often required to be tested for selected food samples. In such applications, any nucleic acid markers for the diseases and pathogens can be amplified and detected using the methods according to this invention. The amplification methods can be used to develop diagnostic methods or procedures in laboratories or alternatively diagnostic and testing kits, which can be built for use in laboratories or points of care or in field locations outside of lab where rapid testing or diagnosis is required.

The following Examples are provided to aid in the understanding of the invention and are not construed as a limitation thereof.

EXAMPLES

Example 1: Amplification and Characterization of a Prothrombin Product A

The sequences of template and primers for prothrombin product A are shown in FIG. 9 and in the following Table 1:

List of human prothrombin gene product A primers

| Type | Name | SEQ ID NO: | sequence | Size (base) |
|---|---|---|---|---|
| DASL, forward | PIA-FII-F2' | 2 | CTCCTCGACGGCCCACCTGCGCAGTCCACCGTCGAGG AGCCTCAATGCTCCCAGT | 55 |

-continued

List of human prothrombin gene product A primers

| Type | Name | SEQ ID NO: | sequence | Size (base) |
|---|---|---|---|---|
| DASL, reverse | PIA-FII-NR2 | 3 | CTCGACGGGCCACGTGCGCAGTCGACCGTCGAGAGAG CTGCCCATGA | 47 |
| Booster | FII-Nbooster | 4 | TGCTCCCAGTGCTA | 14 |
| Displacement forward | FII-NF1 | 5 | GTTCCCAATAAAAGTGAC | 18 |
| Displacement reverse | FII-NR1 | 6 | ACTGGCTCTTCCTGA | 15 |
| Loop | PIA-LP2 | 7 | GGGCCACGTGCCCAGT | 16 |
| Loop | PIA-FII-F2'-LP7 | 8 | CTCGACGGGCCAC | 13 |

Expected monomer product size is 107 bp

Primer concentrations used were 0.2 µM each for FII-NF1 and FII-NR1 (displacement primers), 1 µM FII-Nbooster (booster primer), 2 µM each of PIA-FII-F2' and PIA-FII-NR2, and 1 µM PIA-LP2 and 1 µM PIA-LP7 (loop primers).

Templates for the reactions were either water, or 10 ng human genomic DNA from Human Tumor Cell Line, MCF 7, or 100 ng of the same human genomic DNA.

Enzyme and buffer conditions were: 1× Isothermal Amplification Buffer (20 mM Tris-HCl, 10 mM (NH4)2SO4, 50 mM KCl, 2 mM MgSO4, 0.1% Tween® 20, pH 8.8@25° C. (New England Biolabs, Beverly, Mass.), 1.4 mM dNTPs, 0.8 M betaine (Sigma-Aldrich), total Mg2+ concentration of 3.5 mM and 8 U Bst DNA polymerase (large fragment)/25 µl reaction. After all reagents and DNAs were added, reactions were incubated at 60° C. for 35 or 50 min.

Figure 10:
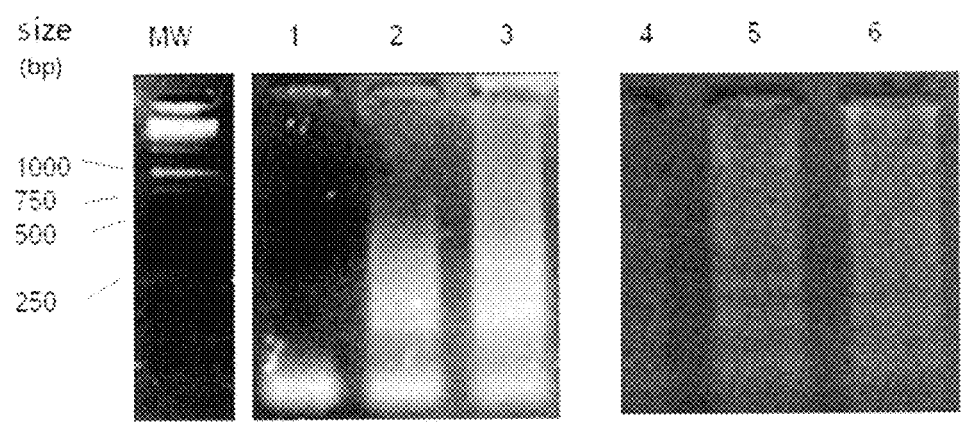
FIG. 10 shows gel electrophoresis results for the preferred DNA amplification of FIG. 9.

1.2% agarose gel electrophoresis was performed on completed reactions. Results are shown in FIG. 10. MW was Fermentas GeneRuler™ 1 kb ladder (Thermo Scientific, Ottawa, Ontario, Canada). Reactions 1 and 4 were water blank. Reactions 2 and 5 had 10 ng of human genomic DNA as template. Reactions 3 and 6 had 100 ng human genomic DNA as template. Incubation conditions were 35 min at 60° C. for reactions 1-3 and 50 min at 60° C. for reactions 4-6. In FIG. 10, note that in Lane 1, the single band appearing at the bottom of the lane is assigned to free unreacted primers. As shown in FIG. 10, both 10 ng and 100 ng of human genomic supported amplification of prothrombin product A in 35 min. In addition, 100 ng human genomic DNA (reactions 3 and 6) produced more DNA products than did 10 ng human genomic DNA (reactions 2, 5). Also, longer reaction time produced more DNA products (lanes 5 and 6 relative to lanes 3 and 4). Blank reactions show no (reaction 1) or little (reaction 4) reaction products. Of note, the reaction 4 products appeared to be different in size and pattern of sizes of products than those of reactions 2, 3 and 4 and 5. For reactions 5 and 6, the products observed ranged from around 60, 100, 200 base pairs (bp) and higher sizes. The booster primerFII-Nbooster and one of the DASL primers PIA-FII-NR2 are expected to produce a 62 bp product. The monomer expected was 107 bp (FIG. 9). One of the dimeric end products according FIG. 6 is expected to be around 206 bp. These predicted sizes of products matched closely with observed bands in size on the agarose gel.

Figure 11:
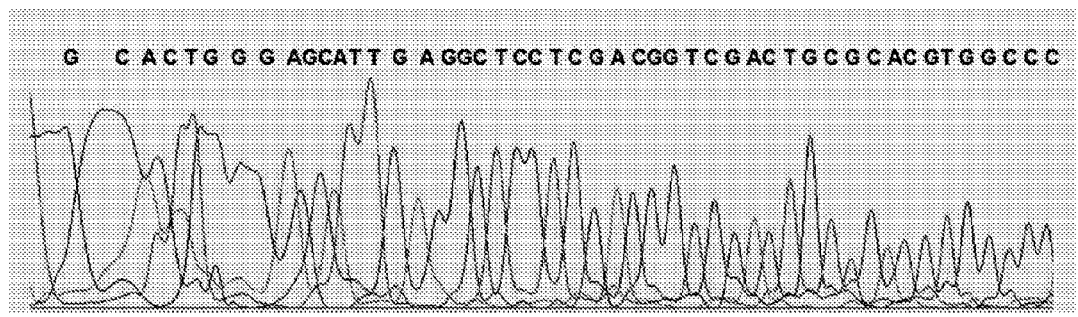
FIG. 11 shows DNA sequencing results for the preferred DNA amplification of FIG. 9.

Reaction 5 was sequenced using the PIA-FII-NR2 (SEQ ID NO 3) primer as the sequencing primer. The results are shown in FIG. 11.

Observed sequence was as follows:

GCACTGGGAGCATTGAGGCTCCTCGACGGTCGACTGCGCACGTGGCCC

For the same region, the expected sequence for comparison with observed sequence is:

GCACTGGGAGCATTGAGGCTC*CTCGACGGTCGACTGCGCACGTGGCCCGT CGAGGAG* (italics: PIA-f2' STEM LOOP)

The observed sequence matched with expected sequence for this construct. Therefore, the correct product was amplified in this experiment.

Estimation of Fold of Amplification in Example 1

We estimated the fold of amplification that occurred in Example 1.

Approximately or up to 100 ng of human genomic DNA was used in the reaction. That is equivalent to 30303 copies of DNA template available for the reaction (see below Table A for the estimation).

Approximately or at least 100 ng of about 100 bp sized of products were obtained, when all products, including the dimers, trimers, tetramers, etc. are were considered. Dimers, trimers, tetramers, polymers are estimated in monomer equivalent quantities. That is equivalent to $9.1 \times 10^{11}$ copies of DNA that was amplified (see below Table A for the estimation).

Therefore, there was about 30 million fold amplification (copies of DNA after amplification divided by copies of DNA before amplification) in the reaction in Example 1.

TABLE A

| | Before Amplification | After Amplification | Fold of Amplification |
|---|---|---|---|
| Copies of DNA | 30303.0 (quantity of DNA per reaction/molecular size of the genome in base pairs/molecular weight per base pair × Avogadro's Constant) | 9.09091E+11 (quantity of DNA per reaction/molecular size of the amplified in base pairs/molecular weight per base pair × Avogadro's Constant) | 30,000,000 |

TABLE A-continued

|  | Before Amplification | After Amplification | Fold of Amplification |
|---|---|---|---|
| Assumptions | a) 100 ng of human DNA genome size is about 3 Gigabytes. b) Each base pair is 660 daltons. c) Avogadro's constant is 6.023 × 10²³ | a) 100 ng of monomer equivalent amplified DNA (estimated by gel) b) monomer is 100 bp in size. Each base pair is 660 daltons. c) Avogadro's constant is 6.023 × 10²³ | |

Example 2: Amplification and Characterization of a Prothrombin Product B

The sequences of template and primers for prothrombin product B are shown in FIG. 12 and in the following Table 2:

mM KCl, 2 mM MgSO4, 0.1% Tween® 20, pH 8.8@25° C. (New England Biolabs), 1.4 mM dNTPs, 0.8 M betaine (Sigma), Mg2+ concentration of 3.5 mM and 8 U Bst DNA polymerase (large fragment)/25 µl reaction. Reactions were incubated at 60° C. for 50 min. The reaction with 100 ng human genomic DNA showed the expected amplified products while the reaction with water did not (data not shown).

Figure 13:
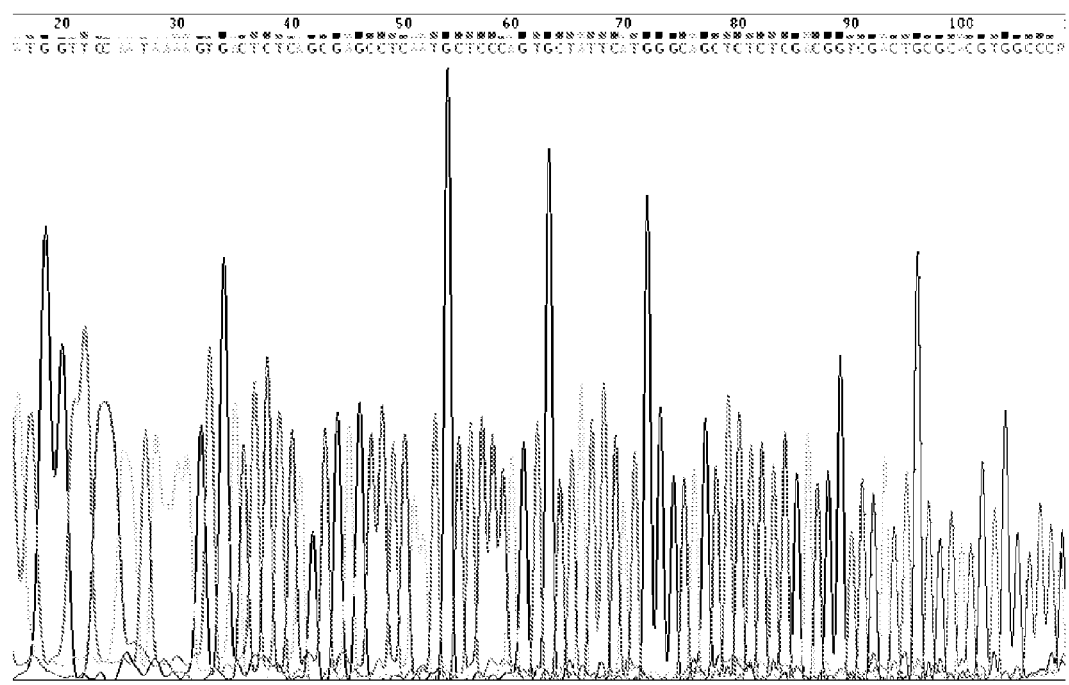
FIG. 13 shows DNA sequencing results for the preferred DNA amplification of FIG. 12.

The reaction with human genomic DNA was diluted and sequenced with sequencing primer FII-SEQ (SEQ ID NO 28). The sequencing results are shown in FIG. 13.

Expected sequence was:

TGGTTCCCAAAAAAGTGACTCTCAGCGAGCCTCAATGCTCCCAGTGCTA
TTCATGGGCAGCTCTCTCGACGGTCGACTGCGCACGTGGCCC.

The observed sequence (FIG. 13) matched with expected sequence, with the exception of the string of CCC (bases 6-8 of expected sequence), was machine auto-read as CC. A manual reading of the chromatogram results suggested a string of CCC, based on spacing of neighboring base peaks, List of human prothrombin gene product B primers

| Type | Name | SEQ ID NO: | sequence | Size (base) |
|---|---|---|---|---|
| DASL, forward | PIA-FII-F2 | 10 | CAGCTCGACGGGCCACGTGCGCAGTCGACCGTCGAG CTGGAACCAATCCCGTGAAA | 56 |
| DASL, reverse | PTA-FII-NR2 | 3 | CTCGACGGGCCACGTGCGCAGTCGACCGTCGAG AGAGCTGCCCATGA | 47 |
| Booster | FII-Nbooster | 4 | TGCTCCCAGTGCTA | 14 |
| Booster | FII-F1' | 11 | CCAATAAAAGTGACTCTCAGC | 21 |
| Displacement forward | FII-F1 | 12 | GGGGCCACTCATATTCTGGGC | 21 |
| Displacement reverse | FII-R1 | 13 | GGTGGTGGATTCTTAAGTCTTC | 22 |
| Loop | PIA-LP2-v2 | 14 | CGAGTTTTACTCGGGGCCACGTGCGCAGT | 29 |

Expected size of a monomer product is 179 bp

Primer concentrations used were 0.4 µM each for FII-F1 and FII-R1 (displacement primers), 1 µM each of FII-Nbooster and FII-F1' (booster primers), 2 µM each of PIA-FII-F2 and PIA-FII-NR2, and 1 µM PIA-LP2 (loop primer).

Templates for the reactions were either water, or 100 ng human genomic DNA. DNA and primer mix was heated at 94° C. for 1 min and cooled on ice before enzyme and buffer were added to the reaction tube.

Enzyme and buffer conditions were: 1x Isothermal Amplification Buffer (20 mM Tris-HCl, 10 mM (NH4)2SO4, 50 suggesting a 100% match between observed and expected sequences (FIG. 13). This confirmed the correct sequence of amplified products.

Example 3: Amplification of Prothrombin Product C Using Various Combination of Primers Sequences for the template and the primers were as in FIG. 14 and in the following Table 3:

List of human prothrombin gene product C primers

| Type | Name | SEQ ID NO: | sequence | Size (base) |
|---|---|---|---|---|
| DASL, forward | PIA-FII-F2' | 2 | CTCCTCGACGGGCCACGTGCGCAGTCGACCGTCGAG GAGCCTCAATGCTCCCAGT | 55 |
| DASL, reverse | PTA-FII-NR2 | 3 | CTCGACGGGCCACGTGCGCAGTCGACCGTCGAG AGAGCTGCCCATGA | 47 |
| Booster | FII-Nbooster | 4 | TGCTCCCAGTGCTA | 14 |

List of human prothrombin gene product C primers

| Type | Name | SEQ ID NO: | sequence | Size (base) |
|---|---|---|---|---|
| Displacement forward | FII-F1 | 12 | GGGGCCACTCATATTCTGGGC | 21 |
| Displacement reverse | FII-R1 | 13 | GGTGGTGGATTCTTAAGTCTTC | 22 |
| Loop | PIA-LP2 | 7 | GGGCCACGTGCGCAGT | 16 |

Expected size of a monomer product is 179 bp

Primer concentrations were 0.2 µM each for FII-F1 and FII-R1 (displacement primers), 1 µM FII-Nbooster (booster primer), 2 µM each of PIA-FII-F2' and PIA-FII-NR2, and 1 µM PIA-LP-V2 (loop primer). The various combinations of primers were used in separate reactions as indicated: "complete"—all primers were present; "–displ primer", "–booster", –"PIA primers", "–loop primer" indicated all primers were present except the name primer(s), which was not added in the corresponding reaction.

Templates for the reactions were either water (blank, "–") or 25 ng human genomic DNA ("+", from Human Tumor Cell Line, MCF 7) as indicated.

Enzyme and buffer conditions were: 1x Isothermal Amplification Buffer (20 mM Tris-HCl, 10 mM (NH4)2SO4, 50 mM KCl, 2 mM MgSO4, 0.1% Tween® 20, pH 8.8@25° C. (New England Biolabs), 1.4 mM dNTPs, 0.8 M betaine (Sigma), Mg2+ concentration of 3.5 mM and 8 U Bst DNA polymerase (large fragment)/25 µl reaction. After all reagents and DNAs were added, reactions were incubated at 60° C. for 40 or 50 min.

Figure 15:
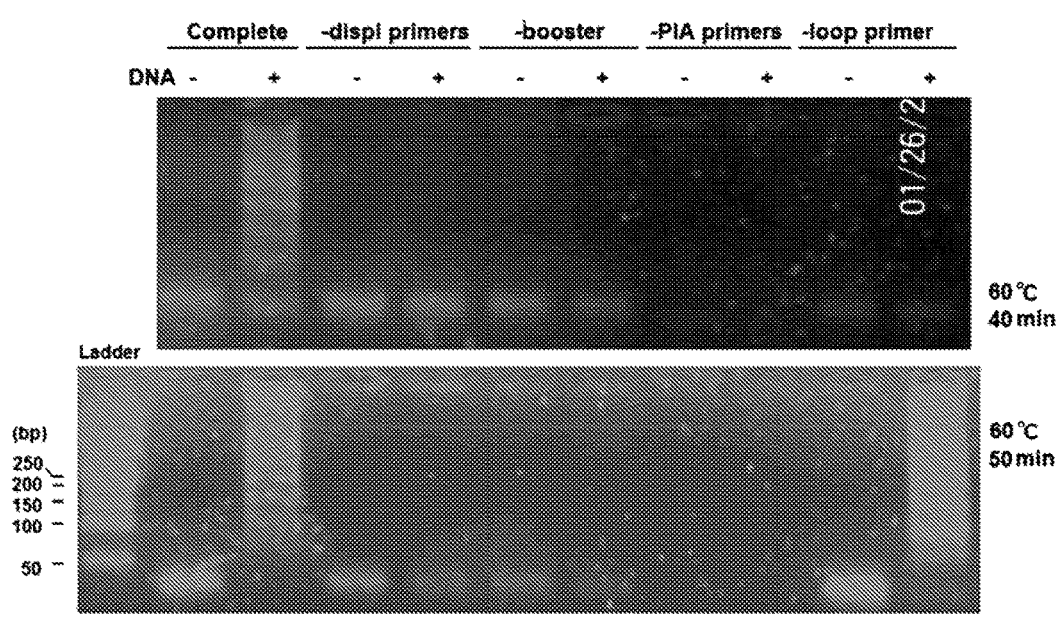
FIG. 15 shows gel electrophoresis results for the preferred DNA amplification of FIG. 14.

1.2% agarose gel electrophoresis was performed. The results are shown in FIG. 15. Note that in Lanes marked with "–", the single band appearing at the bottom of each lane is assigned to free unreacted primers. MW was 100-1000 bp DNA Marker (BioBasic, Markham, Ontario, Canada). Reactions marked with "–" and "+" were water or 25 ng of human genomic DNA as template.

The results (FIG. 15) showed that at 60° C. for 40 min, the reaction was most efficient in the presence all the primers in the "complete" reaction, confirming all the primers were useful in facilitating a specific and efficient reaction. In the absence of loop primer, the reaction proceeded to produce detectable level in 50 min at 60° C.

Example 4: Amplification of Prothrombin Products Using Different Combination of Loop Primers The sequences of the template and primers for prothrombin products are shown in FIG. 16 and in the following Table 4:

List of primers for several human prothrombin gene products

| Type | Name | SEQ ID NO: | sequence | Size (base) |
|---|---|---|---|---|
| DASL, forward | PIA-FII-F2' | 2 | CTCCTCGACGGCCACGTGCGCAGTCGACCGTCGAG GAGCCTCAATGCTCCCAGT | 55 |
| DASL, forward | PTA-FII-F2-Nu | 15 | GGGGGGGAGCTACGGCCTGGTGACGCCCCCC CTGGAACCAATCCCGTGAAA | 51 |
| DASL, reverse | PIA-FII-R2 | 16 | ACTCTCGACGGGCCACGTGCGCAGTCGACCGTCGAG AGTATTACTGGCTCTTCCTGA | 57 |
| DASL, reverse | PIA-FII-R2-Nu | 17 | GGGGGGGAGCTACGGCCTGGTGACGCCCCCC AGTATTACTGGCTCTTCCTGA | 52 |
| DASL, reverse | PIA-FII-NR2 | 3 | CTCGACGGGCCACGTGCGCAGTCGACCGTCGAG AGAGCTGCCCATGA | 47 |
| Booster | FII-Nbooster | 4 | TGCTCCCAGTGCTA | 14 |
| Booster | FII-F1' | 11 | CCAATAAAAGTGACTCTCAGC | 21 |
| Booster | FII-filler-R'B | 18 | AGA GCT GCC CAT GAA TA | 17 |
| Displacement forward | FII-F1 | 12 | GGGGCCACTCATATTCTGGGC | 21 |
| Displacement reverse | FII-R1 | 13 | GGTGGTGGATTCTTAAGTTCTTC | 22 |

List of primers for several human prothrombin gene products

| Type | Name | SEQ ID NO: | sequence | Size (base) |
|---|---|---|---|---|
| Loop | PIA-LP2-v2 | 14 | CGAGTTTTACTCGGGGCCACGTGCGCAGT | 29 |
| Loop | PIA-FII-F2'-LP7 | 8 | CTCGACGGGCCAG | 13 |
| Loop | PIA-LP-Nu1 | 19 | CTC CTT TTT GGA GCT ACG GCC TGG TGA C | 28 |
| Loopp | PIA-LP-Nu2 | 20 | GCTC CTT TTT GGA GCT ACG GCC TGG TGA C | 29 |

Expected Sizes of Monomer Products in Example 3: 132 bp for Reactions 2 and 4; 179 and 174 bp for Reactions 6 and 8.

Primer concentrations were 0.3 µM each for FII-F1 and FII-R1 (displacement primers), and 1 µM PIA-LP2-V2 and 2 µM PIA-LP7 (loop primers), 1 µM FII-filler-R' (reactions 1-6) or 1 µM FII-Nbooster (booster primer), and 1 µM FII-F1' (reactions 7 and 8) were used as booster primers. 2 µM each of the DASL primers are used as follows: PIAFIIF2' and FII-R2-Nu (reactions 1 to 4), PIA-FII-F2, FII-NR2 (reactions 5 and 6), PIA-FII-F2-Nu and PIA-FII-NR2 (reactions 7 and 8). For reactions 1-2, 1 µM PIA-LP-Nu1 was also added as a loop primer for the loop in the primerFII-R2-Nu, and reactions 3-4 and 7-8 1 µM PIA-LP-Nu2 was also added for the loop in the primerFII-R2-Nu and FII-F2-Nu, as additional loop primers.

Templates for the reactions were either water (reactions ("−", 1, 3, 5 and 7), or 100 ng human genomic DNA ("+", reactions 2, 4, 6 and 8).

Enzyme and buffer conditions were: 1x Isothermal Amplification Buffer (20 mM Tris-HCl, 10 mM (NH4)2SO4, 50 mM KCl, 2 mM MgSO4, 0.1% Tween® 20, pH 8.8@25° C. (New England Biolabs), 1.4 mM dNTPs, 0.8 M betaine (Sigma), Mg2+ concentration of 3.5 mM and 6 U Bst 2.0 DNA polymerase (large fragment, New England Biolabs)/25 µl reaction. at 63° C. for 35 or 45 min.

Figure 17:
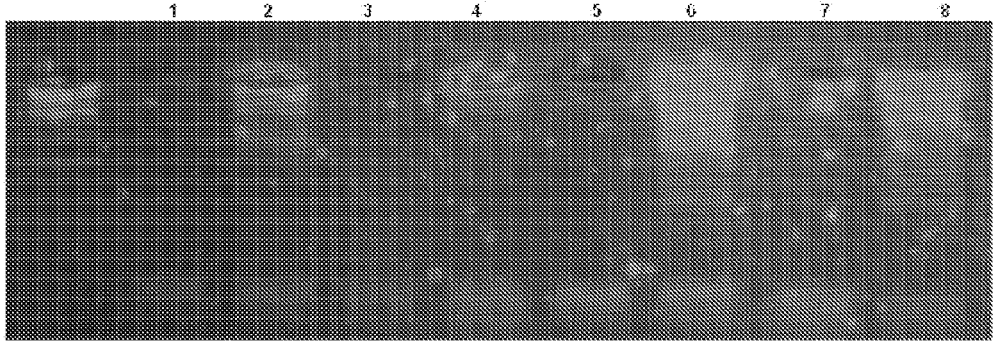
FIG. 17 shows gel electrophoresis results for the preferred DNA amplification of FIG. 16.
Figure 19:
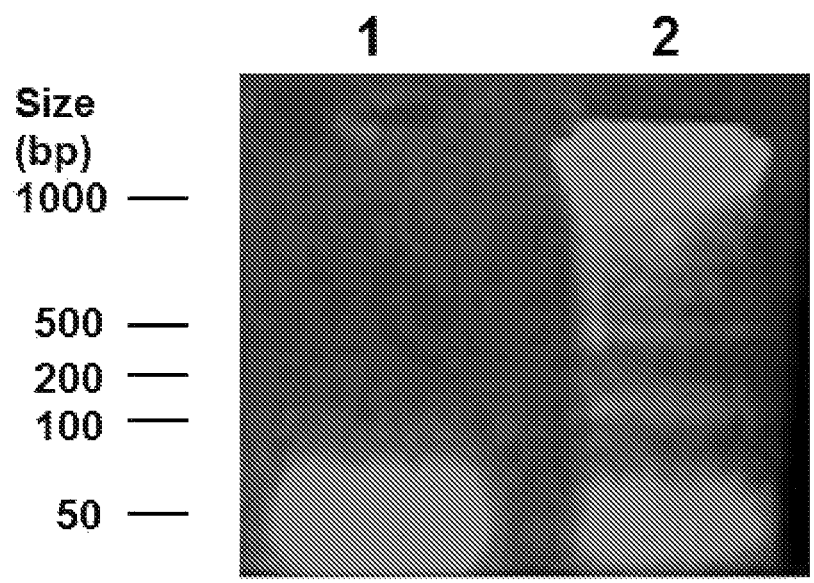
FIG. 19 shows gel electrophoresis results for the preferred DNA amplification of FIG. 18.

1.2% agarose gel electrophoresis was performed. MW was 100-1000 bp DNA Marker (BioBasic, Markham, Ontario, Canada). Reactions loaded are labeled as above described. The results are shown in FIG. 17. Note that in Lanes 1, 3, 5, and 7, the single band appearing at the bottom of the lane is assigned to free unreacted primers.

These results (FIG. 17) showed that whereas a common stem loop structure and a loop primer can be shared for both forward and reverse strands in a DASL reaction (reaction 5 and 6), two different stem loop structures and two different loop primers (reactions 1, 2, 3, 4, 7 and 8) could also be used for the forward and reverse strands in a DASL reaction to support successful amplification.

Example 5: Amplification of a Methylenetetrahydrofolate Reductase (MTHFR) Product The sequences of the template and primers for the methylenetetrahydrofolate reductase (MTHFR) product are shown in FIG. 18 and in the following Table 5:

List of human prothrombin gene product C primers

| Type | Name | SEQ ID NO: | Sequence | Size (base) |
|---|---|---|---|---|
| DASL, forward | PIA-677-F2 | 22 | CTC GAC GG G CCA CGT GCG CAG TCG A CC GTC GAG GGAGCTTTGAGGCTGAC | 50 |
| DASL, reverse | PTA-677-R2' | 23 | CTC GAC GG G CCA CGT GCG CAG TCG A CC GTC GAG CTCAAAGAAAAGCTGCGTG | 52 |
| Booster | 677-booster 1 | 24 | TGAAGCACTTGAAGGAGAAGG | 21 |
| Booster | 677-booster 4 | 25 | CGGGAGCCGATTTCATC | 17 |
| Displacement forward | 677-F1 | 26 | CAGGTTACCCCAAAGGCCAC | 20 |
| Displacement reverse | 677-R1 | 27 | CCATGTCGGTGCATGCCTTC | 20 |
| Loop | PIA-LP2 | 7 | GGGCCACGTGCGCAGT | 16 |

Expected size of a monomer product is 190 bp

Primer concentrations were 0.4 µM each for 677-F1 and 677-R1 (displacement primers), 1 µM each 677-booster 1 and 677-booster 4 (booster primers), 2 µM each of PIA-677-F2 and PIA-677-R2', and 1 µM PIA-LP2 (loop primer). Templates for the reactions were either water, or 100 ng human genomic DNA. Primer-template mix was pre-heated at 94° C. for 1 min and cooled on ice, before the polymerase and buffer master mix were added (see below).

Enzyme and buffer conditions were: 1× Isothermal Amplification Buffer (20 mM Tris-HCl, 10 mM (NH4)2SO4, 50 mM KCl, 2 mM MgSO4, 0.1% Tween® 20, pH 8.8@25° C. (New England Biolabs), 1.4 mM dNTPs, 0.8 M betaine (Sigma-Aldrich), Mg2+ concentration of 3.5 mM and 8 U Bst 2.0 DNA polymerase (large fragment, New England Biolabs)/25 µl reaction. Reactions were incubated at 60° C. for 50 min.

1.2% agarose gel electrophoresis was performed. MW was 100-1000 bp DNA Marker (BioBasic, Markham, Canada). The sizes of DNA size standards are marked. The MW lane is not shown. Reactions were as labeled. Reactions 1 and 2 were water or 20 ng of human genomic DNA as template, respectively. Results (FIG. 19) showed that products were amplified in the template-dependent manner—the reaction 2 with template showed products in regularly increasing multiple band pattern, whereas no product was amplified when the template was absent in the reaction (water as template, reaction 1). Note that in Lane 1, the single band appearing at the bottom of the lane is assigned to free unreacted primers.

Figure 20:
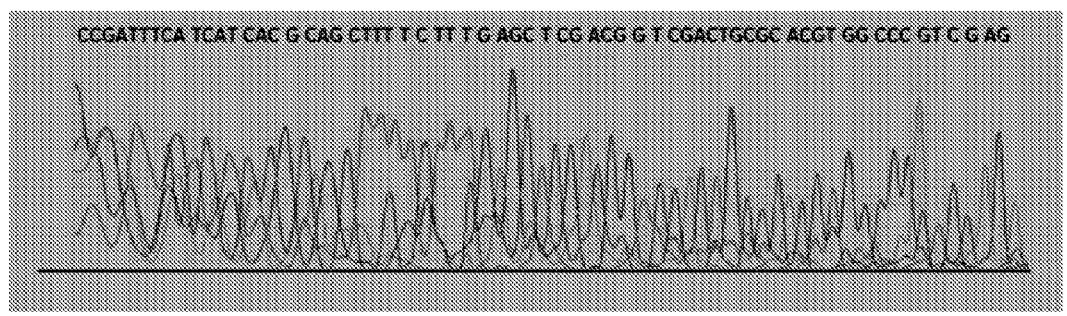
FIG. 20 shows DNA sequencing results for the preferred DNA amplification of FIG. 18.
Figure 21:
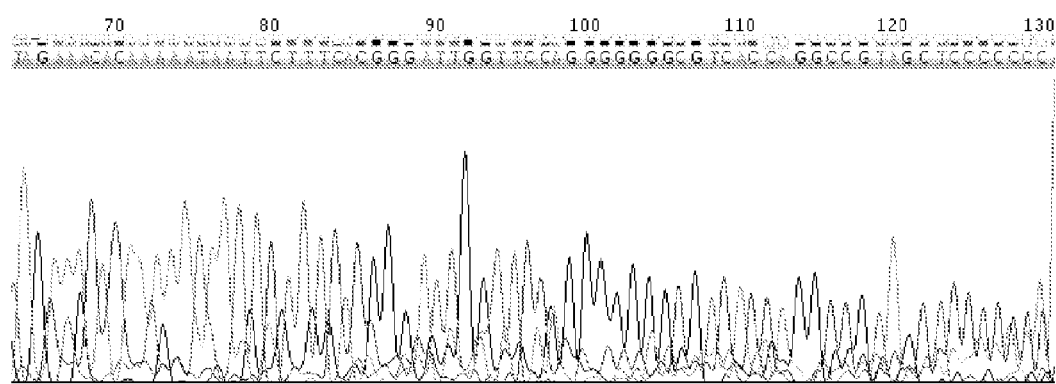
FIG. 21 shows DNA sequencing results for another preferred DNA amplification of the present invention, wherein the target sequence comprises human prothrombin gene fragment B (SEQ ID NO:9).

The reaction #2 with human genomic DNA as template was sequenced with primer"677-booster 1" (SEQ ID NO 24). The results are shown in FIG. 20.

Expected sequence (for the comparison with the same region of observed sequence) is as follows:

CCGATTTCATCATCACGCAGCTTTTCTTTGAG<u>CTCGACGGTCGACTGC GCACGTGGCCCGTCGAG</u>

(The underlined part is the stem loop of PIA-677-R2').

Observed sequence from the automated sequence with manual reading at the beginning of the sequence was:

CCGATTTCATCATCACGCAGCTTTTCTTTGAGCTCGACGGTCGACTGC GCACGTGGCCCGTCGAG

In addition to the correct sequence presented as the predominant chromatogram peaks, there was a background of other sequences presented as minor peaks. This was expected as the reaction products were mixtures of various species as seen on the gel electrophoresis pattern (FIG. 18). Overall, the observed sequence matched with the expected sequence, confirming that the amplified products in reaction 2 had the correct sequence.

Example 6: Amplification of an Amplified Product for a Prothrombin Product

The template for the prothrombin product was the same as the prothrombin product B are shown in FIG. 12, (SEQ ID NO:9). The forward DASL primer was PIA-FII-F2-Nu (SEQ ID NO:15) and the reverse DASL primer was PIA-FII-NR2 (SEQ ID NO:3). No other primers were used.

Primer concentrations were 2 µM each of PIA-FII-F2-Nu and PIA-FII-NR2. Templates for the reactions were either water, or 100 ng human genomic DNA in 19 ul reaction. Primer-template mix was pre-heated at 94° C. for 2 min and cooled on ice, before the enzyme and buffer master mix were added (see below).

Enzyme and buffer conditions were: 1x Isothermal Amplification Buffer (20 mM Tris-HCl, 10 mM (NH4)2SO4, 50 mM KCl, 2 mM MgSO4, 0.1% Tween® 20, pH 8.8@25° C. (New England Biolabs), 1.4 mM dNTPs, 0.8 M betaine (Sigma-Aldrich), Mg2+ concentration of 3.5 mM and 4 U Bst 2.0 DNA polymerase (large fragment, New England Biolabs)/25 µl reaction. Reactions were incubated at 60° C. for 50 min.

The reaction with human genomic DNA as template was sequenced with primer FII-filler-R'B (SEQ ID NO 29). The results are show in FIG. 21.

Expected sequence (for the comparison with the same region of observed sequence) is as follows:

TAGAAACACAAAAATAATTCTTTCACGGGATTGGTTCCAGGGGGGCG TCACCAGGCCGTAGCTCCCCCCC

Observed sequence from the automated sequence with manual reading at the beginning of the sequence was:

TAGAAACACAAAAATAATTCTTTCACGGGATTGGTTCCAGGGGGGCGT CACCAGGCCGTAGCTCCCCCCC.

In addition to the correct sequence presented as the predominant chromatogram peaks, there was a background of other sequences presented as minor peaks. This was expected as the product for sequencing was expected to be a mixture of various sizes monomers and multimers. Overall, the observed sequence matched with the expected sequence, confirming that the amplified products had the correct expected sequence.

The scope of the claims should not be limited by the preferred embodiments set forth in the examples, but should be given the broadest interpretation consistent with the description as a whole.

---

The invention claimed is:

1. A method of amplifying a nucleic acid comprising:
   (a) providing a first template having: (i) a first region comprising a 3' end stem loop; (ii) a second region comprising a 5' end stem loop and (iii) a single stranded target sequence connecting the 3' end stem loop and the 5' end stem loop, said target sequence having a first homology site at the 3' end of the said target sequence, a second homology site at the 5' end of the said target sequence and, optionally, a linking region between the first homology site and the second homology site;
   (b) providing at least two stem loop primers capable of hybridizing at the 3' end to target sequence, a polymerase having strand displacement activity and a reaction buffer; wherein a first stem loop primer has: (i) a 5' end stem loop formed by a third region located 5' terminal and a third complementary region annealing to one another to form a third stem, and a third loop region connecting said third region located 5' terminal and said third complementary region; and (ii) a nucleotide sequence at the 3' terminal complementary to the first homology site; and wherein a second stem loop primer has: (i) a 5' end stem loop formed by a fourth region located 5' terminal and a fourth complementary region annealing to one another to form a fourth stem, and a fourth loop region connecting said fourth region located 5' terminal and said fourth complementary region; and (ii) a nucleotide sequence at the 3' terminal complementary to a sequence which is complementary to the second homology site;
   (c) annealing the first stem loop primer to the first homology site on the first template;
   (d) extending the first stem loop primer along the first template by means of the polymerase having strand displacement activity to form a second template, said second template having: (i) a third homology site complementary to the first homology site; and (ii) a fourth homology site complementary to the second homology site;
   (e) extending the 3' terminal of the first template by means of the polymerase having strand displacement activity, thereby displacing the second template from the first template;
   (f) annealing the second stem loop primer to the fourth homology site on the second template;
   (g) extending the second stem loop primer along the second template by means of the polymerase having strand displacement activity to form a third template;
   (h) extending the 3' terminal of the second template by means of the polymerase having strand displacement activity, thereby displacing the third template from the second template; and
   (i) repeating steps (c) to (h) using the third template as the first template in step (c), thereby amplifying the nucleic acid.

2. The method according to claim 1, further comprising:
   (i) providing a displacement primer, wherein said displacement primer has a nucleotide sequence complementary to a nucleotide sequence upstream or downstream of one or more of said homology sites;
   (ii) annealing the displacement primer to a complementary region upstream or downstream of one of said homology sites;
   (iii) extending the displacement primer by means of the polymerase having strand displacement activity, thereby displacing two of said templates from each other;
   (iv) providing a loop primer, wherein said loop primer has a nucleotide sequence complementary to a nucleotide sequence on one of said loop regions of said stem loops on one of said templates;
   (v) annealing the loop primer to a complementary region on one of said loop regions of said stem loops on one of said templates;
   (vi) extending the loop primer by means of the polymerase having strand displacement activity, thereby facilitating displacement of two of said templates from each other;
   (vii) providing a booster primer, wherein said booster primer has a nucleotide sequence complementary to a nucleotide sequence on said linking region;
   (viii) annealing the booster primer to a complementary region on said linking region; and
   (ix) extending the booster primer by means of the polymerase having strand displacement activity, thereby facilitating displacement of two of said templates from each other.

3. The method according to claim 1, wherein said single stranded target sequence has a length of 70 bases pair or fewer.

4. The method according to claim 1, wherein said 3' end stem loop and said 5' end stem loop of the first template have the same nucleotide sequence.

5. The method according to claim 1, wherein said step (a) of providing said first template comprises:
   (a1) providing a double stranded nucleic acid target, said double stranded nucleic acid target comprising a first strand complementary to a second strand, said second strand having sequences which are the same as the sequences of the third and fourth homology sites;
   (a2) annealing the second stem loop primer to the sequence which is the same as the fourth homology site on the second strand;
   (a3) extending the second stem loop primer along the second strand by means of the polymerase having strand displacement activity to form a third strand, said third strand having sequences which are the same as the sequences of the first and second homology sites, thereby displacing the first strand;
   (a4) annealing the first stem loop primer to the sequence which is the same as the first homology site on the third strand;
   (a5) extending the first stem loop primer along the third strand by means of the polymerase having strand displacement activity to form a fourth strand, said fourth strand having sequences which are the same as the sequences of the third and fourth homology sites, thereby displacing the second strand;
   (a6) annealing the second stem loop primer to the sequence which is the same as the fourth homology site on the fourth strand;
   (a7) extending the second stem loop primer along the fourth strand by means of the polymerase having strand displacement activity to form a fifth strand, said fifth strand having sequences which are the same as the sequences of the first and second homology sites, thereby forming a three strand complex having the third, fourth and fifth strands;
   (a8) allowing the three strand complex to reversibly dissociate into: (i) the third strand; and (ii) a double stranded complex comprising the fourth and fifth strands, wherein one end of the double stranded complex has a 3' end stem loop on the fourth strand and a 5'end stem loop on the fifth strand;
   (a9) extending the 3' terminal of the fourth strand by means of the polymerase having strand displacement activity, thereby displacing the fifth strand, wherein the fifth strand is used as the first template in step (a).

6. The method according to claim 1, wherein each of said third and fourth loop regions are 10 to 30 base pairs in length; and
   wherein each of said third and fourth stems are 4 to 25 base pairs in length.

7. The method according to claim 1, wherein said 5' end stem loops of the first stem loop primer and the second stem loop primer have a melting temperature of 60 degrees Celsius to 80 degrees Celsius.

8. The method according to claim 1, wherein the third complementary region and the third loop region of the first stem loop primer overlap with the nucleotide sequence at the 3' terminal complementary to the first homology site.

9. The method according to claim 1, wherein the third complementary region of the first stem loop primer overlaps with the nucleotide sequence at the 3' terminal complementary to the first homology site; and wherein the fourth complementary region of the first stem loop primer overlaps with the nucleotide sequence at the 3' terminal complementary to a sequence which is complementary to the second homology site.

10. The method according to claim 1, wherein the fourth complementary region and the fourth loop region of the second stem loop primer overlap with the nucleotide sequence at the 3' terminal complementary to a sequence which is complementary to the second homology site.

11. A system for amplifying nucleic acid comprising:
   (a) a first template having: (i) a first region comprising a 3'end stem loop; (ii) a second region comprising a 5' end stem loop; and (iii) a single stranded target sequence connecting the 3' end stem loop and the 5' end stem loop, said target sequence having a first homology site at the 3' end of the target sequence, a second homology site at the 5' end of the target sequence and, optionally, a linking region between the first homology site and the second homology site; and
   (b) at least two stem loop primers, a polymerase having strand displacement activity and a reaction buffer; wherein a first stem loop primer has: (i) a 5' end stem loop formed by a third region located 5' terminal and a third complementary region annealing to one another to form a third stem, and a third loop region connecting said third region located 5' terminal and said third complementary region; and (ii) a nucleotide sequence at the 3' terminal complementary to the first homology site; and wherein a second stem loop primer has: (i) a 5' end stem loop formed by a fourth region located 5' terminal and a fourth complementary region annealing to one another to form a fourth stem, and a fourth loop region connecting said fourth region located 5' terminal and said fourth complementary region; and (ii) a nucleotide sequence at the 3' terminal complementary to a sequence which is complementary to the second homology site.

12. The system according to claim 11, further comprising:
   a displacement primer, wherein said displacement primer has a nucleotide sequence complementary to a nucleotide sequence upstream or downstream of one or more of said homology sites;
   a loop primer, wherein said loop primer has a nucleotide sequence complementary to a nucleotide sequence on one of said loop regions of said stem loops on the first template; and
   a booster primer, wherein said booster primer has a nucleotide sequence complementary to a nucleotide sequence on said linking region.

13. The system according to claim 11, wherein said single stranded target sequence has a length of 70 bases pairs or less.

14. The system according to claim 11, wherein said 3' end stem loop and said 5' end stem loop of the first template have the same nucleotide sequence.

15. The system according to claim 11, wherein each of said third and fourth loop regions are 10 to 30 base pairs in length; and
   wherein each of said third and fourth stems are 4 to 25 base pairs in length.

16. The system according to claim 11, wherein said 5' end stem loops of the first stem loop primer and the second stem loop primer have a melting temperature of 60 degrees Celsius to 80 degrees Celsius.

17. The system according to claim 11, wherein the third complementary region and the third loop region of the first stem loop primer overlap with the nucleotide sequence at the 3' terminal complementary to the first homology site.

18. The system according to claim 11, wherein the third complementary region of the first stem loop primer overlaps with the nucleotide sequence at the 3' terminal complementary to the first homology site.

19. The system according to claim 11, wherein the fourth complementary region and the fourth loop region of the second stem loop primer overlap with the nucleotide sequence at the 3' terminal complementary to a sequence which is complementary to the second homology site.

20. The system according to claim 11, wherein the fourth complementary region of the first stem loop primer overlaps with the nucleotide sequence at the 3' terminal complementary to a sequence which is complementary to the second homology site.

* * * * *

SEQUENCE LISTING

<160> NUMBER OF SEQ ID NOS: 29

<210> SEQ ID NO 1
<211> LENGTH: 93
<212> TYPE: DNA
<213> ORGANISM: Homo sapiens

<400> SEQUENCE: 1
atggttccca ataaaagtga ctctcagcga gcctcaatgc tcccagtgct attcatgggc      60
agctctctgg gctcaggaag agccagtaat act      93

<210> SEQ ID NO 2
<211> LENGTH: 55
<212> TYPE: DNA
<213> ORGANISM: Artificial Sequence

```
<220> FEATURE:
<223> OTHER INFORMATION: Artificially extended primer PIA-FII-F2'

<400> SEQUENCE: 2
ctcctcgacg ggccacgtgc gcagtcgacc gtcgaggagc tcaatgctcc ccagt          55

<210> SEQ ID NO 3
<211> LENGTH: 47
<212> TYPE: DNA
<213> ORGANISM: Artificial Sequence
<220> FEATURE:
<223> OTHER INFORMATION: Artificially extended primer PIA-FII-NR2

<400> SEQUENCE: 3
ctcgacgggc cacgtgcgca gtcgaccgtc gagagagctg cccatga                    47

<210> SEQ ID NO 4
<211> LENGTH: 14
<212> TYPE: DNA
<213> ORGANISM: Artificial Sequence
<220> FEATURE:
<223> OTHER INFORMATION: Artificially extended primer FII-Nbooster

<400> SEQUENCE: 4
tgctcccagt gcta                                                         14

<210> SEQ ID NO 5
<211> LENGTH: 18
<212> TYPE: DNA
<213> ORGANISM: Artificial Sequence
<220> FEATURE:
<223> OTHER INFORMATION: Artificially extended primer FII-NF1

<400> SEQUENCE: 5
gttcccaata aaagtgac                                                     18

<210> SEQ ID NO 6
<211> LENGTH: 15
<212> TYPE: DNA
<213> ORGANISM: Artificial Sequence
<220> FEATURE:
<223> OTHER INFORMATION: Artificially extended primer FII-NR1

<400> SEQUENCE: 6
actggctctt cctga                                                        15

<210> SEQ ID NO 7
<211> LENGTH: 16
<212> TYPE: DNA
<213> ORGANISM: Artificial Sequence
<220> FEATURE:
<223> OTHER INFORMATION: Artificially extended primer PIA-LP2

<400> SEQUENCE: 7
gggccacgtg cgcagt                                                       16

<210> SEQ ID NO 8
<211> LENGTH: 13
<212> TYPE: DNA
<213> ORGANISM: Artificial Sequence
<220> FEATURE:
<223> OTHER INFORMATION: Artificially extended primer PIA-FII-F2'-LP7

<400> SEQUENCE: 8
ctcgacgggc cac                                                          13
```

<210> SEQ ID NO 9
<211> LENGTH: 226
<212> TYPE: DNA
<213> ORGANISM: Homo sapiens

<400> SEQUENCE: 9
tttggagagt aggggggccac tcatattctg ggctcctgga accaatcccg tgaaagaatt    60
atttttgtgt ttctaaaact atggttccca ataaaagtga ctctcagcga gcctcaatgc   120
tcccagtgct attcatgggc agctctctgg gctcaggaag agccagtaat actactggat   180
aaagaagact taagaatcca ccacctggtg cacgctggta gtccga                  226

<210> SEQ ID NO 10
<211> LENGTH: 56
<212> TYPE: DNA
<213> ORGANISM: Artificial Sequence
<220> FEATURE:
<223> OTHER INFORMATION: Artificially extended primer PIA-FII-F2

<400> SEQUENCE: 10
cagctcgacg ggccacgtgc gcagtcgacc gtcgagctgg aaccaatccc gtgaaa         56

<210> SEQ ID NO 11
<211> LENGTH: 21
<212> TYPE: DNA
<213> ORGANISM: Artificial Sequence
<220> FEATURE:
<223> OTHER INFORMATION: Artificially extended primer FII-F1'

<400> SEQUENCE: 11
ccaataaaag tgactctcag c                                               21

<210> SEQ ID NO 12
<211> LENGTH: 21
<212> TYPE: DNA
<213> ORGANISM: Artificial Sequence
<220> FEATURE:
<223> OTHER INFORMATION: Artificially extended primer FII-F1

<400> SEQUENCE: 12
ggggccactc atattctggg c                                               21

<210> SEQ ID NO 13
<211> LENGTH: 22
<212> TYPE: DNA
<213> ORGANISM: Artificial Sequence
<220> FEATURE:
<223> OTHER INFORMATION: Artificially extended primer FII-R1

<400> SEQUENCE: 13
ggtggtggat tcttaagtct tc                                              22

<210> SEQ ID NO 14
<211> LENGTH: 29
<212> TYPE: DNA
<213> ORGANISM: Artificial Sequence
<220> FEATURE:
<223> OTHER INFORMATION: Artificially extended primer PIA-LP2-v2

<400> SEQUENCE: 14
cgagttttac tcggggccac gtgcgcagt                                       29

```
<210> SEQ ID NO 15
<211> LENGTH: 51
<212> TYPE: DNA
<213> ORGANISM: Artificial Sequence
<220> FEATURE:
<223> OTHER INFORMATION: Artificially extended primer PIA-FII-F2-Nu

<400> SEQUENCE: 15
gggggggagc tacggcctgg tgacgccccc cctggaacca atcccgtgaa a            51

<210> SEQ ID NO 16
<211> LENGTH: 57
<212> TYPE: DNA
<213> ORGANISM: Artificial Sequence
<220> FEATURE:
<223> OTHER INFORMATION: Artificially extended primer PIA-FII-R2

<400> SEQUENCE: 16
actctcgacg ggccacgtgc gcagtcgacc gtcgagagta ttactggctc ttcctga      57

<210> SEQ ID NO 17
<211> LENGTH: 52
<212> TYPE: DNA
<213> ORGANISM: Artificial Sequence
<220> FEATURE:
<223> OTHER INFORMATION: Artificially extended primer PIA-FII-R2-Nu

<400> SEQUENCE: 17
gggggggagc tacggcctgg tgacgccccc cagtattact ggctcttcct ga           52

<210> SEQ ID NO 18
<211> LENGTH: 17
<212> TYPE: DNA
<213> ORGANISM: Artificial Sequence
<220> FEATURE:
<223> OTHER INFORMATION: Artificially extended primer FII-filler-R'B

<400> SEQUENCE: 18
agagctgccc atgaata                                                  17

<210> SEQ ID NO 19
<211> LENGTH: 28
<212> TYPE: DNA
<213> ORGANISM: Artificial Sequence
<220> FEATURE:
<223> OTHER INFORMATION: Artificially extended primer PIA-LP-Nu1

<400> SEQUENCE: 19 ctccttttg gagctacggc ctggtgac                                       28

<210> SEQ ID NO 20
<211> LENGTH: 29
<212> TYPE: DNA
<213> ORGANISM: Artificial Sequence
<220> FEATURE:
<223> OTHER INFORMATION: Artificially extended primer PIA-LP-Nu2

<400> SEQUENCE: 20 gctcctttt ggagctacgg cctggtgac                                      29

<210> SEQ ID NO 21
<211> LENGTH: 171
<212> TYPE: DNA
<213> ORGANISM: Homo sapiens
```

```
<400> SEQUENCE: 21
ctattggcag gttaccccaa aggccacccc gaagcaggga gctttgaggc tgacctgaag      60
cacttgaagg agaaggtgtc tgcgggagcc gatttcatca tcacgcagct tttctttgag     120
gctgacacat tcttccgctt tgtgaaggca tgcaccgaca tgggcatcac t              171

<210> SEQ ID NO 22
<211> LENGTH: 50
<212> TYPE: DNA
<213> ORGANISM: Artificial Sequence
<220> FEATURE:
<223> OTHER INFORMATION: Artificially extended primer PIA-677-F2

<400> SEQUENCE: 22
ctcgacgggc cacgtgcgca gtcgaccgtc gagggagctt tgaggctgac                50

<210> SEQ ID NO 23
<211> LENGTH: 52
<212> TYPE: DNA
<213> ORGANISM: Artificial Sequence
<220> FEATURE:
<223> OTHER INFORMATION: Artificially extended primer PIA-677-R2'

<400> SEQUENCE: 23
ctcgacgggc cacgtgcgca gtcgaccgtc gagctcaaag aaaagctgcg tg              52

<210> SEQ ID NO 24
<211> LENGTH: 21
<212> TYPE: DNA
<213> ORGANISM: Artificial Sequence
<220> FEATURE:
<223> OTHER INFORMATION: Artificially extended primer 677-booster 1

<400> SEQUENCE: 24
tgaagcactt gaaggagaag g                                                21

<210> SEQ ID NO 25
<211> LENGTH: 17
<212> TYPE: DNA
<213> ORGANISM: Artificial Sequence
<220> FEATURE:
<223> OTHER INFORMATION: Artificially extended primer 677-booster 4

<400> SEQUENCE: 25
cgggagccga tttcatc                                                     17

<210> SEQ ID NO 26
<211> LENGTH: 20
<212> TYPE: DNA
<213> ORGANISM: Artificial Sequence
<220> FEATURE:
<223> OTHER INFORMATION: Artificially extended primer 677-F1

<400> SEQUENCE: 26
caggttaccc caaaggccac                                                  20

<210> SEQ ID NO 27
<211> LENGTH: 20
<212> TYPE: DNA
<213> ORGANISM: Artificial Sequence
<220> FEATURE:
<223> OTHER INFORMATION: Artificially extended primer 677--R1

<400> SEQUENCE: 27
ccatgtcggt gcatgccttc                                                  20
```

```
<210> SEQ ID NO 28
<211> LENGTH: 18
<212> TYPE: DNA
<213> ORGANISM: Artificial Sequence
<220> FEATURE:
<223> OTHER INFORMATION: Artificially extended primer FII-SEQ

<400> SEQUENCE: 28
ctggaaccaa tcccgtga                                                    18

<210> SEQ ID NO 29
<211> LENGTH: 17
<212> TYPE: DNA
<213> ORGANISM: Artificial Sequence
<220> FEATURE:
<223> OTHER INFORMATION: Artificially extended primer FII-filler-R'B

<400> SEQUENCE: 29
agagctgccc atgaata                                                     17
```